United States Patent
Walker et al.

(10) Patent No.: US 7,366,675 B1
(45) Date of Patent: Apr. 29, 2008

(54) METHODS AND APPARATUS FOR INCREASING, MONITORING AND/OR REWARDING A PARTY'S COMPLIANCE WITH A SCHEDULE FOR TAKING MEDICINES

(75) Inventors: Jay S. Walker, Ridgefield, CT (US); Magdalena Mik, Greenwich, CT (US); Michiko Kobayashi, Stamford, CT (US); Geoffrey M. Gelman, Stamford, CT (US); Russell Pratt Sammon, Stamford, CT (US); Andrew P. Golden, New York, NY (US)

(73) Assignee: Walker Digital, LLC, Stamford, CT (US)

( * ) Notice: Subject to any disclaimer, the term of this patent is extended or adjusted under 35 U.S.C. 154(b) by 1475 days.

(21) Appl. No.: 09/609,017

(22) Filed: Jun. 30, 2000

Related U.S. Application Data

(60) Provisional application No. 60/188,279, filed on Mar. 10, 2000.

(51) Int. Cl.
   *G06Q 10/00* (2006.01)
   *G06Q 50/00* (2006.01)
   *G07F 11/00* (2006.01)
(52) U.S. Cl. .................. 705/2; 221/2; 221/1
(58) Field of Classification Search .......... 705/2, 705/3, 1; 600/300; 128/903, 904; 221/1, 221/2, 9; 700/244, 231; 455/421
See application file for complete search history.

(56) References Cited

U.S. PATENT DOCUMENTS

| | | | |
|---|---|---|---|
| 4,588,303 A | 5/1986 | Wirtschafter et al. | |
| 4,682,299 A | 7/1987 | McIntosh et al. | ........... 264/569 |
| 4,782,966 A | 11/1988 | Thackrey | |
| 4,899,839 A | 2/1990 | Dessertine et al. | |
| 5,210,785 A | 5/1993 | Sato et al. | ..................... 379/58 |
| 5,589,838 A | 12/1996 | McEwan | ..................... 342/387 |
| 5,600,706 A | 2/1997 | Dunn et al. | ................... 379/59 |
| 5,678,182 A | 10/1997 | Miller et al. | ............... 455/33.1 |

(Continued)

FOREIGN PATENT DOCUMENTS

EP    0 526 166 A2    7/1992

(Continued)

OTHER PUBLICATIONS

"Electronic monitoring gains more acceptance: formerly clunky devices now cheap, user-friendly; devices to track medication compliance", American Health Consultants Inc. Aids Alert: Feb. 1998, No. 2, vol. 13, p. 21, ISSN: 0887-0292.*

(Continued)

*Primary Examiner*—Igor N. Borissov
(74) *Attorney, Agent, or Firm*—Walker Digital Management, LLC

(57) ABSTRACT

Methods and apparatus are provided for increasing and/or for monitoring a party's compliance with a schedule for taking medicines. In a first embodiment, a method is provided that includes receiving information regarding whether at least two medicine containers were able to communicate during a pre-determined time period, and determining a level to which the party complied to a medicine schedule based on the information. The method further includes rewarding the party based on the party's level of compliance. Systems, apparatus and computer program products are provided for carrying out the above-described embodiments and numerous other embodiments.

34 Claims, 18 Drawing Sheets

U.S. PATENT DOCUMENTS

| | | | |
|---|---|---|---|
| 5,678,571 A | 10/1997 | Brown | |
| 5,758,288 A | 5/1998 | Dunn et al. | 455/456 |
| 5,768,382 A | 6/1998 | Schneier et al. | |
| 5,800,264 A | 9/1998 | Pascal et al. | |
| 5,828,751 A | 10/1998 | Walker et al. | |
| 5,867,821 A | 2/1999 | Ballantyne et al. | |
| 5,911,132 A | 6/1999 | Sloane | 705/3 |
| 5,969,678 A | 10/1999 | Stewart | 342/457 |
| 5,970,143 A | 10/1999 | Schneier et al. | |
| 6,018,289 A | 1/2000 | Sekura et al. | 340/309.4 |
| 6,070,761 A | 6/2000 | Bloom et al. | 222/81 |
| 6,167,362 A | 12/2000 | Brown et al. | |
| 6,259,654 B1 | 7/2001 | de la Huerga | 368/10 |
| 6,484,027 B1 | 11/2002 | Mauney et al. | 455/421 |
| 6,689,103 B1 | 2/2004 | Palasis | 604/173 |

FOREIGN PATENT DOCUMENTS

| | | | | |
|---|---|---|---|---|
| GB | 2240543 A | * | 8/1991 | |
| JP | 403256876 A | * | 11/1991 | 221/2 |
| WO | WO 95/09386 A1 | | 4/1995 | |
| WO | WO 95/26009 A1 | | 9/1995 | |

OTHER PUBLICATIONS

"Clever containers", Electronics Times: Sep. 6, 1999, p. 31.*

Office Action mailed Jan. 17, 2007 for U.S. Appl. No. 09/609,253, 18 pp.

Office Action mailed Jan. 18, 2006 for U.S. Appl. No. 09/609,253, 10 pp.

Office Action mailed Dec. 30, 2004 for U.S. Appl. No. 09/609,253, 20 pp.

Office Action mailed Apr. 7, 2004 for U.S. Appl. No. 09/609,253, 28 pp.

Office Action mailed Jul. 17, 2003 for U.S. Appl. No. 09/609,253, 36 pp.

PCT International Search Report for Application No. PCT/US99/21895 dated Apr. 19, 2000, 3 pp.

Bruce Schneier, Applied Cryptography 2$^{nd}$ Edition, Chapter 2, 27 pp.

Paul Amos, Robert Kubasak "Drug Cards Manage Rising Prescription Costs", Personal Journal, May 1993, 6 pp.

Peter Ognibene "Smart Cards Could Save Lives-and Dollars" Health Care: A Computerized Personal Medial Record Would Assist Doctors and Avert Dangerous Errors, The Los Angeles Times, Apr. 12, 1993, 2 pp.

Anonymous, Patient Financial Incentives for Compliance, Feedback Suggested by Medco Exec: Expanded Use of Questionnaires in Disease Management Program Planned, FDC Reports: The Pink Sheet, Sep. 19, 1994, 4 pp.

Lowell C. Brown et al. "Computerized Patient Records - CPR and the Law: Plan Now", Dec. 1992, 6 pp.

Daniel C. Morris, "The Ten Basics of System Security", Computers in Healthcare, Nov. 1989, 3 pp.

Robert F. Pendrak et al. "Information Technologies Need to Protect Patient Confidentiality", Oct. 1998, 3 pp.

Elizabeth Gardner, "Computer Dilemma: Clinical Access vs. Confidentially", Nov. 1989, 6 pp.

* cited by examiner

| PATIENT ID 308 | NAME 310 | ADDRESS 312 | TELEPHONE NUMBER 314 | PHYSICIAN 316 | REWARD PROGRAM 318 |
|---|---|---|---|---|---|
| P-123-45-6789 | JANE DOE | 115 MAIN ST. SPRINGFIELD, USA | (203) 325-0895 | BENJAMIN SPOCK | YES |
| P-111-22-3333 | JACK FROST | 21 JUMP ST. NOWHERE, USA | (415) 925-9331 | ROBERT LIVINGSTONE | NO |
| P-321-12-3443 | SAM SPADE | 13 ELM ST. GOTHAM, USA | (501) 629-0888 | ELIZABETH BLACKWELL | YES |

| PATIENT ID: P-123-45-6789 | | | 402 |
|---|---|---|---|
| PRESCRIPTION ID 412 | PRESCRIPTION STATUS 414 | START DATE 416 | END DATE 418 |
| R-102-365 | ACTIVE | 12/25/2002 | 06/25/2003 |
| R-198-342 | ACTIVE | 01/01/2003 | 03/05/2003 |
| R-208-119 | CLOSED | 06/24/2002 | 07/01/2002 |
| R-315-239 | ACTIVE | 02/15/2003 | 04/15/2003 |

| REWARD ID 512 | REWARD FOR COMPLIANCE 514 |
|---|---|
| A | $100 OFF NEXT BILL |
| B | 50% OFF ALL COPAYS FOR 1 YEAR |
| C | ENTRY INTO $1M SWEEPSTAKES |
| D | $100 |
| E | 1 FREE DOCTOR'S VISIT |

FIG. 5

| PATIENT ID 608 | TIME CODE DUE 610 | TIME CODE RECEIVED 612 | CODE STATUS 614 | REWARD ID 616 |
|---|---|---|---|---|
| P-123-45-6789 | 02/15/2003 23:59 | 02/15/2003 20:15 | 95% COMPLIANCE | D |
| P-321-12-3443 | 02/16/2003 12:00 | -- | NOT YET DUE | C |
| P-235-71-1131 | 02/14/2003 23:59 | -- | OVERDUE 0% COMPLIANCE | A |

FIG. 6

PATIENT ID: P-123-45-6789 _802_

CONTAINER ID: C-562-891 _804_

PRESCRIPTION ID: R-102-365 _806_

PRESCRIPTION RULES: ONE PILL TO BE TAKEN 3 TIMES A DAY AT 6 HOUR INTERVALS _808_

START TIME: 02/15/2003 00:00                        END TIME: 02/15/2003 23:59 _810_

| CONTAINER ID _828_ | PRESCRIPTION ID _830_ | RULES _832_ | RULES COMPLIANCE _834_ | PROXIMITY START TIME _836_ | PROXIMITY END TIME _838_ | PROXIMITY COMPLIANCE _840_ |
|---|---|---|---|---|---|---|
| C-152-906 | R-198-342 | -2 HOURS | 100% | 02/15/2003 00:00 | 02/15/2003 08:00 | 100% |
| C-152-906 | R-198-342 | -2 HOURS | 100% | 02/15/2003 08:05 | 02/15/2003 14:00 | 100% |
| C-152-906 | R-198-342 | -2 HOURS | 100% | 02/15/2003 14:30 | 02/15/2003 16:00 | 85% |
| C-295-149 | R-315-239 | -- | N/A | 02/15/2003 15:45 | 02/15/2003 20:00 | 100% |
| C-152-906 | R-198-342 | -2 HOURS | 100% | 02/15/2003 16:05 | 02/15/2003 20:00 | 85% |
| C-295-149 | R-315-239 | +2 HOURS | N/A | 02/15/2003 20:10 | 02/15/2003 23:59 | 85% |
| C-152-906 | R-198-342 | -- | 100% | 02/15/2003 20:10 | 02/15/2003 23:59 | 100% |
| C-521-0811 | R-208-119 | -- | N/A | -- | -- | N/A |

METHODS AND APPARATUS FOR INCREASING, MONITORING AND/OR REWARDING A PARTY'S COMPLIANCE WITH A SCHEDULE FOR TAKING MEDICINES

CROSS-REFERENCE TO RELATED U.S. APPLICATIONS

This application claims priority from U.S. Provisional Patent Application Ser. No. 60/188,279, filed Mar. 10, 2000, the content of which is hereby incorporated by reference herein in its entirety.

This application is related to U.S. patent application Ser. No. 09/165,089, filed Oct. 1, 1998, titled "Method and Apparatus For Documenting Cap Removal Data", now U.S. Pat. No. 6,751,730 B1, the content of which is hereby incorporated by reference herein in its entirety.

This application also is related to U.S. patent application Ser. No. 09/609,253, filed Jun. 30, 2000 (titled "Methods and Apparatus for Increasing and/or for Monitoring a Party's Compliance with a Schedule for Taking Medicines") the content of which is hereby incorporated by reference herein in its entirety.

FIELD OF THE INVENTION

The present invention relates generally to healthcare, and more specifically to methods and apparatus for increasing and/or for monitoring a party's compliance with a schedule for taking medicines.

BACKGROUND OF THE INVENTION

The deleterious consequences of a patient's failure to comply with a prescribed schedule for taking one or more medicines (i.e., patient non-compliance) have long been recognized, and are predominantly manifested in terms of human costs and monetary costs. Human costs associated with patient non-compliance include, for example, poor health, death, a lengthened healing process and/or the emergence of new and drug-resistant strains of viruses/bacteria. Accompanying medical costs include, for example, hospitalization expenses, surgery expenses and/or increased insurance expenses. A seven thousand person per year death rate of Americans and a $100 billion annual toll on the American healthcare system have been attributed to patient non-compliance (see, the November 1999 report of the Institute of Medicine of the National Academy of Sciences, and Healthcare PR & Marketing News, vol. 8, no. 18, Sep. 2, 1999, respectively).

The main reasons for patient non-compliance are well known. Patient non-compliance occurs, for example, because a patient forgets to take one or more medicines, forgets to abide by various rules for taking one or more medicines, misinterprets rules for taking one or more medicines, or does not want to take one or more medicines (e.g., because taking the medicines is a nuisance, because of adverse side effects associated with one or more medicines, etc.). Also, patient non-compliance may occur because a patient does not feel that one or more medicines are necessary (e.g., because the patient feels better, because the patient does not feel any immediate effects of taking/not taking a medicine, because a medicine is merely a preventative medicine such as hypertension medication, etc.), because the patient cannot afford the medicine, because the patient runs out of medicine before obtaining a refill, or the like.

Patient non-compliance typically becomes more pronounced when a patient takes many medicines. For example, a schedule for taking six medicines is more difficult to adhere to than a schedule for taking only two medicines. The dangers and/or the risks associated with patient non-compliance also increase with the number of medicines to be taken (e.g., due to potential adverse medicine interactions amongst the medicines).

To combat patient non-compliance, numerous conventional techniques/systems have been employed. For example, as an attempt at preventing a customer from taking incompatible medicines, a pharmacy may track prescribed medicines that the pharmacy fills for the customer. Likewise, a doctor may track each medicine that the doctor prescribes for a patient. However, pharmacists and doctors have difficulty tracking the actual consumption of medicines and/or encouraging adherence to a medicine schedule (e.g., because pharmacists/doctors typically do not meet with customer/patients on a daily basis).

Other conventional techniques/systems for combating patient non-compliance include, for example, medicine containers that communicate with a central device to provide reminders and warnings to patients regarding when medicines should or should not be taken, devices that dispense one or more medicines at a time and then issue reminders/warnings to patients regarding the dispensed medicines, etc. Other conventional devices may record patient compliance information (e.g., when a medicine was taken) and may communicate (or allow a patient to communicate) such information to a healthcare facility or insurance company (e.g., to allow the healthcare facility or insurance company to monitor patient compliance). For example, previously incorporated U.S. patent application Ser. No. 09/165,089, filed Oct. 1, 1998, which is now U.S. Pat. No. 6,751,730 B1, discloses a system that documents and authenticates cap removal data (e.g., the number of times that a patient removes the cap of a medicine container), so that the cap removal data may be reliably provided to a third party (e.g., an insurance company).

Despite the prevalence of techniques/systems for combating patient non-compliance and for monitoring patient non-compliance, patient non-compliance remains a significant drain on the healthcare industry. Accordingly, a need exists for improved methods and apparatus for increasing and/or for monitoring a party's compliance with a schedule for taking medicines.

SUMMARY OF THE INVENTION

To overcome the drawbacks of the prior art, novel methods and apparatus are provided for increasing and/or for monitoring a party's compliance with a schedule for taking medicines. In a first embodiment, a novel method is provided for use by a first container that is adapted to store a first medicine. The method includes storing information regarding the first medicine and wirelessly communicating a signal between the first container and a second container adapted to store a second medicine. As used herein "wirelessly" communicating means communicating without the use of a physical connection such as an electrical wire (e.g., via a radio frequency (RF) signal).

In one or more embodiments, the method may further include: (1) transmitting information regarding the first medicine from the first container to the second container and/or transmitting information regarding the second medicine from the second container to the first container; (2) receiving information regarding a schedule for taking at least one of the first medicine and the second medicine; (3) detecting if a portion of the first medicine has been removed from the first container and/or detecting if a portion of the second medicine has been removed from the second container; (4) detecting if a party attempts to take the first medicine within a predetermined time period of taking the second medicine (and vice versa) and generating a warning if the first medicine is incompatible with the second medicine; (5) transmitting an indicator of the warning to at least one of a representative of an insurance company, a representative of a pharmacy and a representative of a medical facility; (6) generating at least one code based at least in part on the signal communicated between the first and the second containers, the at least one code indicating whether at least one party has complied with a schedule for taking the first medicine and the second medicine; and/or (7) outputting the at least one code to at least one of a representative of an insurance company, a representative of a pharmacy and a representative of a medical facility. Accordingly, in at least one embodiment of the invention, one or more containers for storing one or more medicines (i.e., medicine containers) may generate a warning if a party attempts to take incompatible medicines together (or within a predetermined time period of one another). Also, one or more medicine containers may notify a representative of an insurance company, a representative of a pharmacy, a representative of a medical facility or any other entity if a party has complied with (or has failed to comply with) a schedule for taking medicines. As used herein, a "representative" may be, for example, any person (e.g., an employee, a subcontractor, an agent, an objective third party, etc.) or any communications device (e.g., a computer, a facsimile machine, a telephone, a pager, etc.).

In a second embodiment, a method is provided that includes determining if a first container for storing a first medicine is positioned so as to wirelessly communicate with a second container for storing a second medicine. The method further includes generating data based at least in part on whether the first container is positioned so as to wirelessly communicate with the second container.

In a third embodiment, a method is provided that includes receiving a signal and, based at least in part on the received signal, determining whether a first container for storing a first medicine was positioned so as to wirelessly communicate with a second container for storing a second medicine.

In a fourth embodiment, a method is provided that includes receiving a signal from a device that monitors whether a first container for storing a first medicine and a second container for storing a second medicine are positioned so as to communicate. The method further includes determining if at least one party has complied with a schedule for taking the first medicine and the second medicine based at least in part on the received signal.

In a fifth embodiment, a method is provided for rewarding a party for complying with a medicine schedule. The method includes receiving information regarding whether at least two medicine containers were able to communicate during a pre-determined time period, and determining a level to which the party complied to a medicine schedule based on the information. The method further includes rewarding the party based on the party's level of compliance.

Systems, apparatus and computer program products are provided for carrying out the above-described embodiments and numerous other embodiments of the present invention. Each computer program product described herein may be carried by a medium readable by a computer (e.g., a carrier wave signal, a floppy disc, a hard drive, a random access memory, etc.).

In one or more embodiments, an apparatus is provided for monitoring whether a party has complied with a schedule for taking medicines. The apparatus includes first storage means for storing a first medicine and means for wirelessly communicating a signal between the first storage means and second storage means for storing a second medicine.

With these and other advantages and features of the invention that will become hereinafter apparent, the nature of the invention may be more clearly understood by reference to the following detailed description of the invention, to the appended claims and to the several drawings attached herein.

BRIEF DESCRIPTION OF THE DRAWINGS

The present invention is described with reference to the accompanying drawings. In the drawings, like reference numbers indicate identical or functionally similar elements.

FIG. 3 illustrates a sample of the contents of a patient database of the controller of FIG. 2;

FIG. 4 illustrates a sample of the contents of a prescription database record of a prescription database of the controller of FIG. 2;

FIG. 5 illustrates a sample of the contents of a reward database of the controller of FIG. 2;

FIG. 6 illustrates a sample of the contents of a compliance database of the controller of FIG. 2;

FIG. 8 illustrates a sample of the contents of a container database record of a container database of the compliance monitoring devices of FIGS. 7A and 7B.

DETAILED DESCRIPTION OF THE INVENTION

Figure 1A:
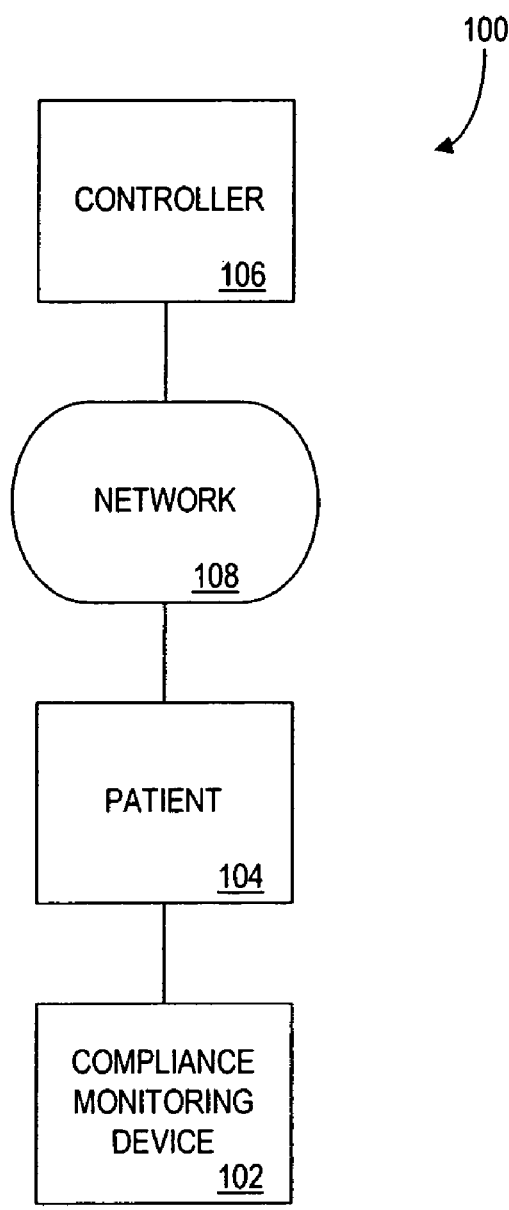
FIG. 1A is a schematic diagram of a novel compliance system for increasing a party's compliance to a medicine schedule and for monitoring the party's compliance to a medicine schedule.

The present invention provides a novel compliance system that can increase a party's compliance to a schedule for taking medicines ("a medicine schedule") and that allows the party's compliance to the medicine schedule to be easily monitored. Novel methods, apparatus and computer program products also are provided.

Relevant Terminology

As used herein, the term "medicine" refers to any prescription or non-prescription medication, dietary supplement, herbal remedy, vitamin, mineral, etc. A medicine may be in any state of matter (e.g., solid, liquid, gas or any combination thereof) and may include a combination of one or more medicines. A medicine may be "taken" by any known mechanism (e.g., oral consumption, injection, transdermally, etc.), and a party may "take" a medicine whether or not the medicine is delivered by the party (e.g., a patient may "take" a medicine if the medicine is injected into the patient by a third party, whether or not the patient is conscious). A container for storing a medicine may include any suitable container (e.g., a pill bottle, a pill box, a vial, a syringe, a foil packet, etc.).

Overview of the Inventive Compliance System

As stated, the inventive compliance system can increase a party's compliance to a medicine schedule and allow the party's compliance to the medicine schedule to be easily monitored. For example, an insurance company may employ one or more embodiments of the invention to receive authenticated information regarding a patient's compliance to a medicine schedule, to track (e.g., monitor over time) the patient's compliance to the medicine schedule and/or to reward the patient based on the level to which the patient complies with the medicine schedule (e.g., so as to motivate the patient to comply through use of positive reinforcement). Numerous rewarding schemes are provided such as monetary rewards, multi-tiered rewards (e.g., different rewards based on the type of compliance a patient exhibits as described below), prizes, etc.

As will be described below with reference to FIGS. 9-13, any indicator (or any number of indicators) of compliance may be monitored and/or tracked with the present invention. For example, an insurance company may monitor a party's compliance with a schedule for taking one medicine, a party's compliance with a schedule for taking multiple medicines, a party's compliance with a requirement that two or more medicine containers be kept within a certain distance or range of one another (e.g., a "proximity requirement"), that multiple parties have satisfied any of the above-described compliance requirements, and/or any other compliance requirements.

Specific embodiments of the invention aid a party in complying with a medicine schedule by: (1) notifying the party when the party should take one or more medicines (e.g., so as to satisfy the medicine schedule) or should not take one or more medicines (e.g., because one or more medicines are incompatible and may harm the party if taken together); (2) reminding the party to obtain a refill of a medicine if the party has consumed all or most of the medicine; and/or (3) assisting the party in locating a medicine container (e.g., if the party has misplaced the medicine container).

In one or more embodiments of the invention, a party obtains a plurality of medicine containers that are capable of wirelessly communicating with one another, that each store a medicine, and that are each programmed with information regarding the medicine stored within the medicine container. Other information such as medicine compatibility information also may be stored within each medicine container as described below with reference to FIG. 7A and FIG. 8. For example, each medicine container may be programmed with all of the information necessary for the medicine container to be "self-regulating" (e.g., by communicating with other medicine containers). That is, in at least one embodiment of the invention, each medicine container may communicate information to other medicine containers that indicates when medicine was removed from the medicine container, each medicine container may receive information that indicates when medicine was removed from other medicine containers, and each medicine container may determine, based on a schedule for taking medicines and/or based on incompatibility information about medicines, whether a party should take a medicine stored within the medicine container. For "self-regulating" medicine containers, an insurance company may track compliance to a medicine schedule merely by monitoring whether the medicine containers are being kept together.

As an example of the use of "self-regulating" medicine containers, assume that a doctor prescribes three medicines to a patient, and that the patient obtains the three medicines from a local pharmacy. When the pharmacy fills the prescriptions for the three medicines, instead of employing a conventional "pill bottle" for each medicine, the pharmacy employs three of the inventive, self regulating medicine containers to store each prescribed medicine. Exemplary embodiments of such self regulating medicine containers are described below with reference to FIG. 7A.

In addition to placing each medicine in each medicine container, the pharmacy "programs" each medicine container with information regarding the medicine to be stored within the container (e.g., via RF communications, via a serial or parallel port, or via any other means as described below with reference to FIG. 7A). The information programmed/stored within each medicine container may include, for example, a schedule for taking the medicine stored within the medicine container, information regarding the compatibility/incompatibility of the medicine stored within the medicine container relative to the other two medicines and/or any other medicines taken by the patient, and any other relevant information. Thereafter, the three medicine containers may communicate amongst one another, exchanging information such as when each medicine stored within each medicine container should be taken, is about to be taken, is being taken or has been taken, and alerting the patient when the patient should take each medicine (e.g., to comply with a medicine schedule) or should not take each medicine (e.g., due to incompatibility amongst two or more of the medicines).

One of the medicine containers may serve as a "compliance monitoring device" that monitors/tracks, for example, the proximity of the medicine containers (e.g., whether the medicine containers are positioned so as to communicate), each time a party takes a medicine, the dose of each medicine taken by a party, etc. Alternatively, a separate central monitoring device (e.g., a device that does not function as a medicine container) may be employed as a compliance monitoring device to monitor/track the above information.

After obtaining the above information, the compliance monitoring device may provide data to a controller (e.g., employed by the insurance company) that includes, for example, (1) information regarding the proximity of the medicine containers (e.g., the times the medicine containers were separated and could not communicate, the times the medicine containers were together and could communicate, etc.); (2) one or more levels to which a party has complied with a proximity requirement for the medicine containers (e.g., a proximity requirement set by an insurance company, such as a pre-determined, maximum time period that the medicine containers may be separated); (3) information regarding the medicines taken by a party (e.g., the amount of each medicine taken by the party, the time each medicine was taken by the party, etc.); and/or (4) one or more levels to which a party has complied with one or more schedules for taking the medicines stored within the medicine containers (e.g., a level to which the party has complied with a schedule for taking each medicine, a level to which the party has complied with a schedule for taking multiple medicines, etc.).

Depending on the data received by the controller, the controller may reward the party directly (e.g., if the data provided by the compliance monitoring device includes one or more levels of compliance that were determined by the compliance monitoring device), or the controller may employ the received data to determine one or more levels of compliance for the party (and may then reward the party).

Note that the present invention provides numerous advantages over the prior art. Through use of one or more embodiments of the present invention, the probability that a party will comply with a schedule for taking medicines may be increased and the party's compliance to a schedule for taking medicines may be easily monitored. Unlike conventional compliance devices, any number of medicine containers configured in accordance with the present invention may be in communication (e.g., as ports or other interfaces for interconnecting medicine containers and/or for connecting a central monitoring device to medicine containers are not required). A highly scalable "compliance system" thereby may be formed through use of the present invention.

In embodiments wherein each medicine container may communicate with a plurality of other medicine containers, communications between medicine containers may continue even if one or more medicine containers malfunction. Likewise, because each medicine container may be in communication with numerous medicine containers, malfunctioning medicine containers are easily identified (e.g., as more than one medicine may detect when a medicine container is malfunctioning). Because medicine containers need not be (but may be) physically interconnected or physically connected to a central monitoring device, malfunctioning medicine containers may be easily replaced.

Specific embodiments of the invention encrypt proximity and/or compliance data that may be provided to an insurance company. In this manner, the insurance company receives "authenticated" data that cannot be falsified (e.g., by a patient). Other embodiments of the invention allow an insurance company to monitor a party's compliance to a medicine schedule merely by monitoring whether two or more medicine containers were able to communicate during a pre-determined time period.

To provide a "positive incentive" for a party to comply to a medicine schedule, embodiments of the invention allow an insurance company, a doctor, a pharmacist or any other relevant entity to conveniently monitor the party's compliance to the medicine schedule (e.g., by monitoring the proximity of two or more medicine containers that may communicate with one another), and to reward the party based on a level to which the party complies with the medicine schedule.

Exemplary Embodiments of the Inventive Compliance System

FIG. 1A is a schematic diagram of a novel compliance system 100 for increasing a party's compliance to a schedule for taking medicines (i.e., a medicine schedule) and for monitoring the party's compliance to the medicine schedule. The novel compliance system 100, and the other systems described herein, are described primarily with reference to a patient's compliance to a prescribed medicine schedule (e.g., a schedule prescribed by a physician) and to the monitoring of the patient's compliance to the prescribed medicine schedule by a representative of an insurance company. However, it will be understood that the present invention may be employed to affect any party's compliance to any medicine schedule, and that monitoring may be performed by a family member, by a representative of a pharmacy, by a representative of a medical facility and/or by any other party/representative.

With reference to FIG. 1A, the novel compliance system 100 includes a compliance monitoring device 102 in communication with a patient 104, and a controller 106 in communication with the patient 104 via a network 108. Although only one compliance monitoring device and only one patient are shown in FIG. 1A, it will be understood that any number of compliance monitoring devices may be employed, that any number of patients (or other parties) may employ each compliance monitoring device, and/or that any number of patients/parties may be in communication with the controller 106.

Figure 1B:
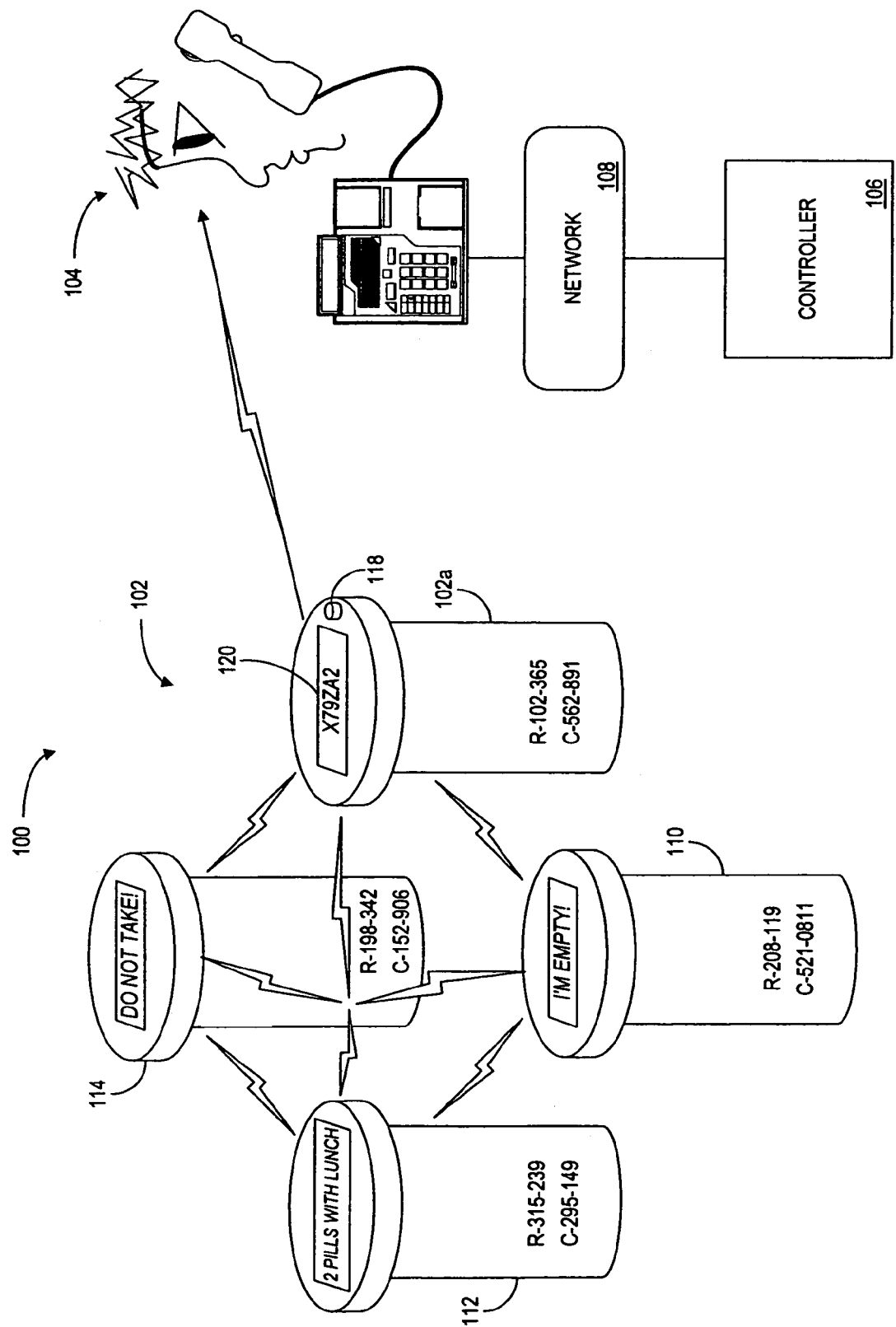
FIG. 1B illustrates an embodiment of the novel compliance system of FIG. 1A wherein a compliance monitoring device of the novel compliance system is a medicine container.

As described below with reference to FIGS. 1B-1E and FIGS. 7A and 7B, the compliance monitoring device 102 may comprise: (1) a medicine container that is in communication with the patient 104 and/or with the controller 106 and that may be in wireless communication with one or more other medicine containers; or (2) a central monitoring device that is in communication with a medicine container (wherein the medicine container may be in wireless communication with one or more other medicine containers). For example, FIG. 1B illustrates a first embodiment of the novel compliance system 100 wherein the compliance monitoring device 102 is a first medicine container 102a that is in wireless communication with a plurality of other medicine containers 110-114. The compliance monitoring device 102/medicine container 102a, and the other medicine containers 110-114, are in visual communication with the patient 104 (e.g., the compliance monitoring device 102/first medicine container 102a displays a code (described below) that indicates a level of compliance of the patient 104 to a schedule for taking the medicines that are stored within the containers 102a and 110-114, the second medicine container 110 displays a message that indicates that the second medicine container 110 is empty and must be refilled, the third medicine container 112 displays a message that indicates that two of the pills stored within the third medicine container 112 should be taken with lunch and the fourth medicine container 114 displays a message that indicates that the medicine stored within the fourth medicine container 114 should not be taken at the present time because the medicine is incompatible with another medicine recently taken or to be taken by the patient 104). The compliance monitoring device 102/medicine container 102a, and the other medicine containers 110-114, similarly may be in communication with the patient 104 via audio means, tactile means, etc.

Figure 1C:
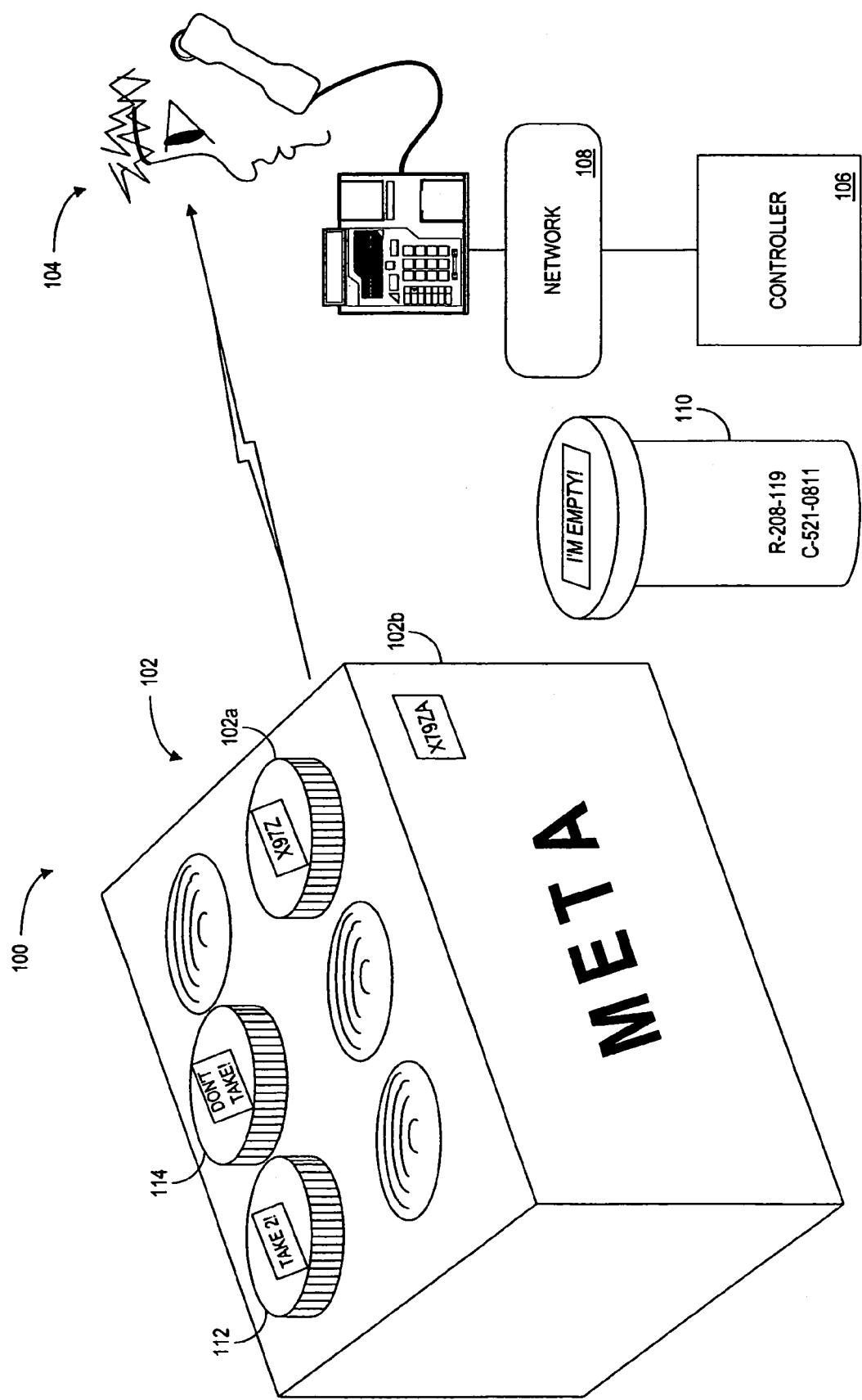
FIG. 1C illustrates an embodiment of the novel compliance system of FIG. 1A wherein a compliance monitoring device of the novel compliance system is a meta-container.

FIG. 1C illustrates a second embodiment of the novel compliance system 100 wherein the compliance monitoring device 102 is a first central monitoring device (referred to as a "meta-container 102b") that may: (1) communicate with a plurality of medicine containers (e.g., medicine containers 102a, 112, 114, etc.); (2) monitor when each medicine container is removed from the meta-container 102b; (3) monitor when each medicine container is returned to the meta-container 102b; (4) store various information regarding the medicine within each medicine container that is in communication with the meta-container 102b; (5) store information regarding the compatibility of the medicines within the medicine containers that are in communication with the meta-container 102b; and/or (6) perform any of the other compliance related functions described below. An exemplary embodiment for the meta-container 102b is described below with reference to FIG. 7B.

Figure 1D:
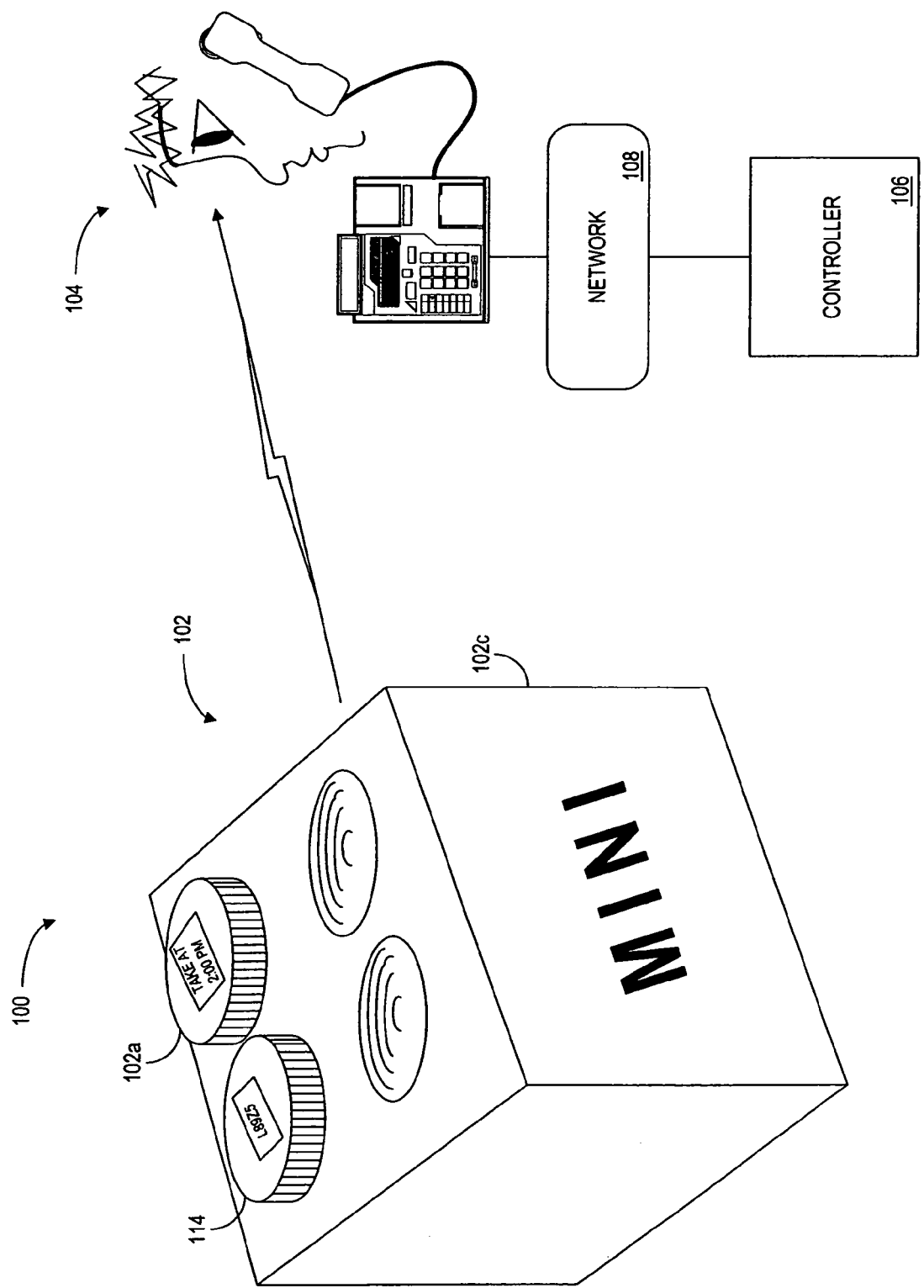
FIG. 1D illustrates an embodiment of the novel compliance system of FIG. 1A wherein a compliance monitoring device of the novel compliance system is a mini-container.

FIG. 1D illustrates a third embodiment of the novel compliance system 100 wherein the compliance monitoring device 102 is a second central monitoring device (referred to as a "mini-container 102c") that may perform many, if not all, of the functions of the meta-container 102b of FIG. 1C while being more portable (e.g., so that the patient 104 may take the mini-container 102c to work, on vacation, etc.). In at least one embodiment, the meta-container 102b and the mini-container 102c may communicate (e.g., via one or more RF transmissions or via any other means such as by exchanging a removable, flash memory device between the meta-container 102b and the mini-container 102c or by having the meta-container 102b and the mini-container 102c "plug" into each other). In this manner, if the patient 104 keeps the mini-container 102c near the meta-container 102b, the meta-container 102b may communicate schedules for taking medicines, times for taking medicines, etc., to the mini-container 102c as described further below. An exemplary embodiment for the mini-container 102c is described below with reference to FIG. 7B.

Those skilled in the art will understand that devices in communication with each other need only be "capable of" communicating with each other and need not be continually transmitting data to or receiving data from each other. On the contrary, such devices need only transmit data to or receive data from each other as necessary, and may actually refrain from exchanging data most of the time. For example, a device in communication with another device via the Internet may not transmit data to the other device or receive data from the other device for weeks at a time. Further, devices may be in communication even though steps may be required to establish a communication link (e.g., dialing a network service provider, placing a medicine container within "range" of another medicine container and/or a central monitoring device, etc.).

The controller 106 may comprise, for example, a computer at an insurance company or at a medical facility, or may comprise an authentication server (e.g., a server that "authenticates" compliance data), as described below with reference to FIG. 2. The network 108 may comprise, for example, a telephone network such as a publicly switched telephone network (PSTN), a cable network, an intranet, an extranet, the Internet, an Internet-based telephone network, or any other communication medium (e.g., a radio frequency link, a microwave link, an optical link, etc.).

Figure 1E:
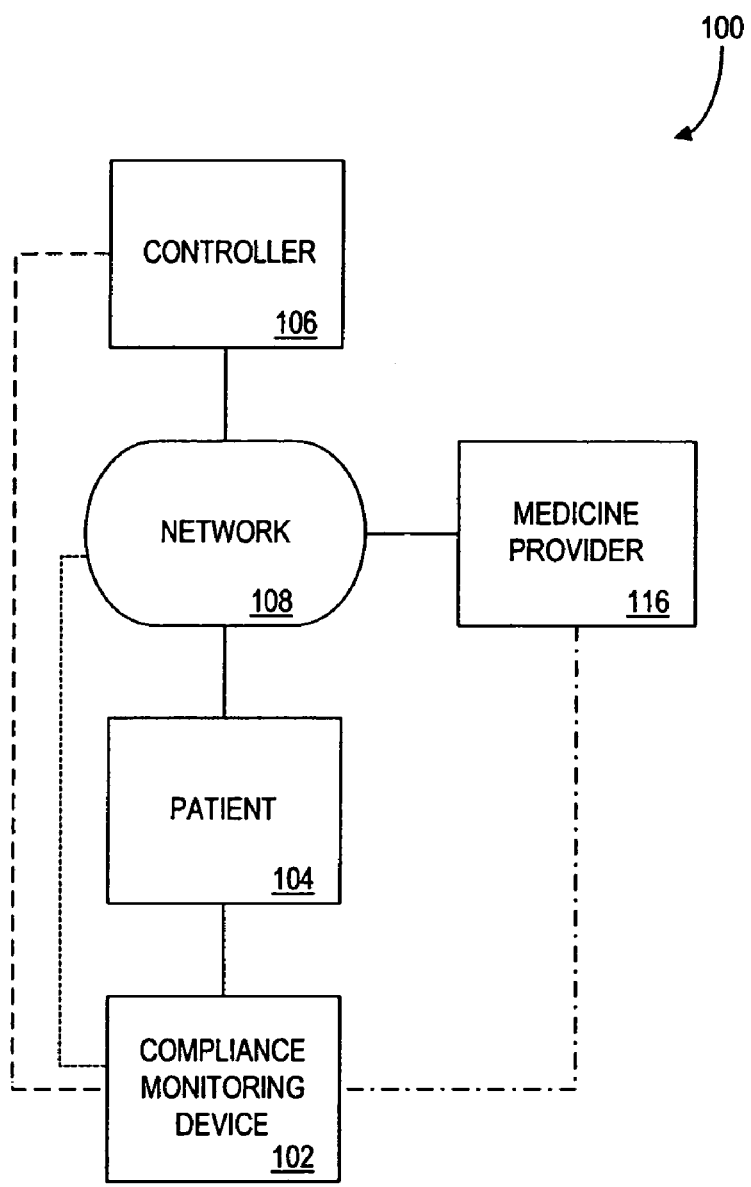
FIG. 1E illustrates an embodiment of the novel compliance system of FIG. 1A wherein a compliance monitoring device of the novel compliance system may be in communication with a controller of the novel compliance system.

While the novel compliance system 100 of FIGS. 1A-1D illustrates "serial-type" communication between the compliance monitoring device 102 and the controller 106, wherein the compliance monitoring device 102 communicates with the patient 104, and the patient 104 communicates with the controller 106, it will be understood that the compliance monitoring device 102 also may be in communication with the controller 106 as shown in FIG. 1E. For example, the compliance monitoring device 102 may be in communication with the controller 106 via the network 108 or via a direct communication link (e.g., if the controller 106 is operated by an insurance company, the controller 106 and/or the insurance company may program the compliance monitoring device 102 with information regarding any medicines the compliance monitoring device 102 monitors/contains, and/or the insurance company may supply the compliance monitoring device 102 to the patient 104).

The compliance monitoring device 102 also may be in communication with one or more medicine providers (e.g., one or more pharmacies) such as a medicine provider 116, either via the network 108 or via a direct communication link (e.g., the medicine provider 116 may program the compliance monitoring device 102 with information regarding any medicines the compliance monitoring device 102 monitors/contains and may supply the compliance monitoring device 102 to the patient 104). Likewise, the patient 104 may bring the compliance monitoring device 102 to the medicine provider 116 for refilling, the medicine provider 116 may obtain compliance data (or proximity information) from the compliance monitoring device 102 (as described below), and the medicine provider 116 may communicate the obtained data/information to the controller 106 (e.g., via the network 108 or by any other communications medium). One or more medicine containers configured in accordance with the present invention similarly may be in communication with the controller 106 and/or with the medicine provider 116.

Exemplary embodiments of the novel compliance system 100 are described below with reference to FIGS. 2-13.

Exemplary Embodiments for the Controller 106

Figure 2:
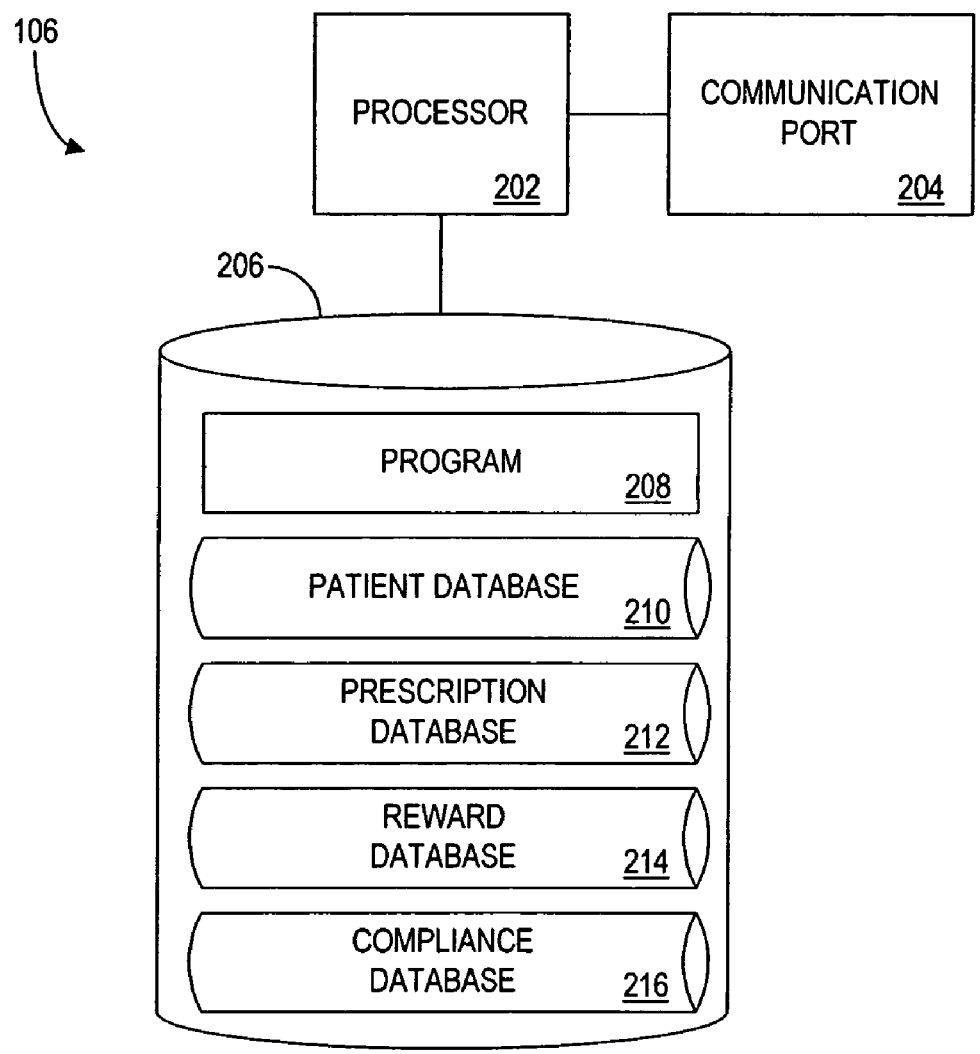
FIG. 2 is a schematic diagram of an exemplary embodiment of a controller of the novel compliance system of FIGS. 1A-1E.

FIG. 2 is a schematic diagram of an exemplary embodiment of the controller 106 of FIGS. 1A-1E. The controller 106 may be implemented as a system controller, as a dedicated hardware circuit, as an appropriately programmed general purpose computer, or as any other equivalent electronic, mechanical or electro-mechanical device.

The controller 106 comprises a processor 202, such as one or more conventional microprocessors (e.g., one or more Intel® Pentium® processors). The processor 202 is in communication with a communication port 204 through which the processor 202 communicates with other devices/parties (e.g., the compliance monitoring device 102, the patient 104 and/or the medicine provider 116). The communication port 204 may include multiple communication channels for simultaneous communication with, for example, the compliance monitoring device 102, with one or more other compliance monitoring devices (not shown), with the patient 104, with one or more other parties (not shown), with the medicine provider 116, and/or with the one or more other medicine providers (not shown). As stated, devices in communication with each other need not be continually transmitting to each other. On the contrary, such devices need only transmit to each other as necessary, may actually refrain from exchanging data most of the time, and may require several steps to be performed to establish a communication link between the devices.

The processor 202 also is in communication with a data storage device 206. The data storage device 206 may comprise an appropriate combination of magnetic, optical and/or semiconductor memory, and may include, for example, Random Access Memory (RAM), Read-Only Memory (ROM), a compact disc and/or a hard disk. The processor 202 and the data storage device 206 each may be, for example, located entirely within a single computer or other computing device; or connected to each other by a communication medium, such as a serial port cable, a telephone line or a radio frequency transceiver. Alternatively, the controller 106 may comprise one or more computers that are connected to a remote server computer (not shown) for maintaining databases.

In an embodiment wherein the controller 106 is employed by (e.g., is operated by) an insurance company, the data storage device 206 may store, for example, (i) a program 208 (e.g., computer program code and/or a computer program product) adapted to direct the processor 202 in accordance with the present invention, and particularly in accordance with the processes described in detail hereinafter with regard to the controller 106; (ii) a patient database 210 adapted to store information regarding patients that are associated with the insurance company (e.g., patients that have an insurance policy from the insurance company); (iii) a prescription database 212 adapted to store information regarding one or more medicines that have been prescribed to a patient (e.g., one or more "prescriptions" of the patient) (e.g., whether a prescription is "active" or "closed", a start date for a prescription, an end date for a prescription, etc.); (iv) a reward database 214 adapted to store a list of rewards that are available to a patient if the patient complies with a schedule for taking medicines; and (v) a compliance database 216 adapted to store information regarding at least one level to which a patient has complied with a schedule for taking medicines (i.e., at least one compliance level). The controller 106 may be similarly configured for use by a medical provider, by a medical facility, etc.

The program 208 may be stored in a compressed, an uncompiled and/or an encrypted format, and may include computer program code that allows the controller 106 to:

1. receive a code from the patient 104 (or from the compliance monitoring device 102) that indicates: (1) that the patient 104 has complied with a schedule for taking medicines (e.g., by indicating a level of compliance); (2) that two or more medicine containers (configured in accordance with the present invention so that the two or more medicine containers may wirelessly communicate) have been kept within a predetermined distance of one another during a pre-determined time period (e.g., that the two or more medicine containers have complied with a "proximity requirement"); and/or (3) any other compliance or proximity information (as described below);
2. decrypt the code if the code is encrypted;
3. determine a level of compliance based on the code (e.g., if the code merely indicates proximity information regarding two or more medicine containers, compute a level of compliance based on the proximity information); and
4. select a reward for the patient 104 based on the determined level of compliance.

The computer program code required to implement the above functions can be easily developed by a person of ordinary skill in the art, and is not described in detail herein. The controller 106 may include any peripheral devices (e.g., telephone keypads, handsets, headsets, microphones, speakers, keyboards, computer displays, etc.) required to implement the above functionality. The program 208 also may include program elements such as an operating system, a database management system and "device drivers" that allow the processor 202 to interface with computer peripheral devices (e.g., a video display, a keyboard, a mouse, etc.).

Note that instructions of the program 208 may be read into a main memory (not shown) of the processor 202 from a computer-readable medium other than the data storage device 206, such as from a ROM or from a RAM. While execution of sequences of instructions in program 208 causes processor 202 to perform the process steps described herein, hard-wired circuitry may be used in place of, or in combination with, software instructions for implementation of the processes of the present invention. Thus, embodiments of the present invention are not limited to any specific combination of hardware and software.

The processor 202 also may be in communication with a clock (not shown) that supplies time and date information to the processor 202 and that may comprise, for example, a clock internal to the processor 202, a clock external to the processor 202 or a clock embodied within the program 208 (e.g., based on a system clock not shown).

Samples of the contents of the patient database 210, of the prescription database 212, of the reward database 214 and of the compliance database 216 are shown in FIGS. 3-6, respectively. The specific data and fields illustrated in these figures represent only one embodiment of the records stored in the databases of the invention. The data and fields of these databases, as well as the number of databases, can be readily modified, for example, to include more or fewer data fields. A single database also may be employed. Note that in the databases of the controller 106 and in the databases of the compliance monitoring device 102 (described below), a different reference numeral is employed to identify each field of each database. However, in at least one embodiment of the invention, fields that are similarly named (e.g., patient identification fields, reward identification fields, etc., described below) store similar or the same data in a similar or in the same data format.

The patient database 210 contains information related to patients that are associated with an insurance company that employs the controller 106. FIG. 3 illustrates a sample of the contents of the patient database 210. As shown in FIG. 3, the patient database 210 contains patient information related to three patients identified in record 302, record 304 and record 306, respectively. Specifically, for each patient associated with the insurance company (e.g., for each patient that has an account/policy with the insurance company), the patient database 210 contains records having fields corresponding to, for example, (1) a patient identifier (ID) 308, used by the controller 106 to identify the patient; (2) a patient name 310; (3) a patient address 312; (4) a patient telephone number

314; (5) a physician 316; and (6) an indication of whether the patient is a participant in a reward program operated by the insurance company (described below). Other patient information not shown in FIG. 3 which may be stored within the patient database 210 includes any information relevant to the controller 106's operations.

Note that the patient database 210 (and the prescription database 212, the reward database 214 and the compliance database 216) may be populated with data provided to the controller 106 via the communication port 204, and that the data may be provided to the controller 106 from the patient 104, from a representative of the patient 104 (e.g., from a family member), from the compliance monitoring device 102, from an insurance company, from a pharmacy or from any other party. The databases (described below) of the compliance monitoring device 102 similarly populated.

The prescription database 212 contains information related to prescriptions of the patients identified in the patient database 210. FIG. 4 illustrates a sample of the contents of an exemplary record 212a of the prescription database 212 that contains information related to the prescriptions of a patient 402 (e.g., patient ID P-123-45-6789, which is Jane Doe of Springfield as identified by record 302 in FIG. 3). As shown in FIG. 4, the prescription database record 212a contains information for four prescriptions of the patient 402 identified in sub-record 404, sub-record 406, sub-record 408 and sub-record 410, respectively. Specifically the prescription database record 212a contains sub-records having fields corresponding to, for example, (1) a prescription identifier (ID) 412 used by the controller 106 to identify each prescription associated with the patient 402 (e.g., each prescription to be taken by, each prescription that is being taken by and/or each prescription that was taken by the patient 402); (2) a prescription status 414 for each prescription (e.g., "active" if the prescription is currently being taken, "pending" if the prescription is to be taken or "closed" if the prescription is no longer being taken); (3) a start date 416 on which the patient 402 began taking each prescription; and (4) an end date 418 on which the patient 402 stopped taking each prescription. Other prescription information not shown in FIG. 4 which may be stored within the prescription database record 212a, within the prescription database 212 or within any other database includes, for example:

(1) the identity of each medicine (e.g., the medicine's generic name, the medicine's brand name, an identifying code for the medicine, etc.);
(2) the name of the pharmaceutical company that manufactures each medicine;
(3) the prescribed method for taking each medicine (e.g., the time of day the medicine should be taken, the number of times a day the medicine should be taken, whether the medicine should be taken with food, the appropriate dose of the medicine to be taken, a time interval the patient should wait between doses, a duration of time the patient should take the medicine, etc.);
(4) the purpose of each medicine (e.g., to lower blood pressure, to thin the blood, to lower cholesterol, to reduce depression, etc.);
(5) interactions of each medicine with other medicines (e.g., other medicines that are part of a medicine schedule of the patient, whether the interactions are adverse or synergistic, etc.);
(6) the cost of each medicine; and
(7) the amount of each medicine that was dispensed to the patient (e.g., the number of pills, the net weight of the dispensed medicine, etc.).

The reward database 214 contains information related to rewards that are available to a patient (identified in the patient database 210) if the patient complies to a schedule for taking medicines. FIG. 5 illustrates a sample of the contents of the reward database 214. As shown in FIG. 5, the reward database 214 contains information for five rewards associated with the controller 106 (e.g., offered by an insurance company that employs the controller 106). The five rewards are identified in records 502-510, respectively. Specifically the reward database 214 contains records having fields corresponding to, for example, (1) a reward identification (ID) 512 used by the controller 106 to identify each reward associated with the controller 106; and (2) a reward 514 identified by each reward identifier 512. As described below, whether a patient receives one of the rewards identified in records 502-510 depends on a level (e.g., 100%, 80%, 92%, etc.) to which the patient complies to a schedule for taking medicines (e.g., a schedule for taking the prescriptions identified for each patient in the prescription database 212). The requisite level of compliance may be, for example, pre-determined (e.g., by an insurance company) and embodied within computer program code of the program 208, or may be stored within a database (e.g., within the compliance database 216 as described below). Likewise (as described further below), a patient may receive one or more of the rewards identified in records 502-510 merely by satisfying a proximity requirement (e.g., established by an insurance company) for two or more medicine containers. For example, because the medicine containers 102a, 110, 112 and 114 may communicate with each other (e.g., communicate information such as when medicines were taken or are to be taken) and may issue alerts/warnings about when to take or not to take medicines, keeping the medicine containers together during a pre-determined time period (e.g., at all times, during time periods when one or more medicines are to be taken, etc.) may ensure that a patient has complied with a medicine schedule.

Note that the rewards identified in records 502-510 are merely exemplary and that any other rewards may be similarly employed. For example, other rewards may include a lower insurance premium, a lower insurance deductible, a lower insurance co-pay, a reimbursement of the cost of a medicine, a prize (e.g., a vacation, a membership at a local gym, etc.), points (e.g., an alternate currency that is redeemable for a prize if enough points are collected), discounts on products (e.g., coupons for products), any of the rewards described in previously incorporated U.S. patent application Ser. No. 09/165,089, filed Oct. 1, 1998, which is now U.S. Pat. No. 6,751,730 B1, or any other reward.

In one or more embodiments of the invention, at least one of a patient, an insurance company and a medical professional (e.g., a doctor) may select a patient's reward from one of the rewards present in the reward database 214. If a patient's reward is "pre-selected" by the patient, by an insurance company or by a medical professional, the patient database 210 may include a field for each patient record that identifies the reward (e.g., by the reward ID 512) selected by or for the patient.

The compliance database 216 contains information related to at least one level to which a patient has complied with a schedule for taking medicines. FIG. 6 illustrates a sample of the contents of the compliance database 216. As shown in FIG. 6, the compliance database 216 contains compliance information for three patients identified in record 602, record 604 and record 606, respectively (e.g., the patients identified in records 302-306 of the patient database 210). Specifically, the compliance database 216 contains records having fields corresponding to, for example, (1) a patient identifier (ID) 608 for each patient; (2) a time 610 by which the controller 106 is to receive (e.g., from each patient) a code that identifies at least one of whether the patient has complied with a schedule for taking medicines and whether the patient has satisfied a proximity requirement for two or more medicine containers configured in accordance with the present invention so that the two or more medicine containers may communicate; (3) a time 612 that identifies when a code was received for/from each patient; (4) a code status 614 that identifies whether a code was received for each patient, whether the patient has complied with a schedule for taking medicines (e.g., as determined by the controller 106 based on the received code) and/or a compliance level for the patient; and (5) a reward ID 616 that identifies a reward selected for each patient (e.g., selected by the patient, by an insurance company or by a medical professional). In the compliance database 216 of FIG. 6, the reward ID 616 of each record 602-606 is one of the reward identifiers specified in the reward database 214.

Exemplary Embodiments for the Compliance Monitoring Device 102

Figure 7A:
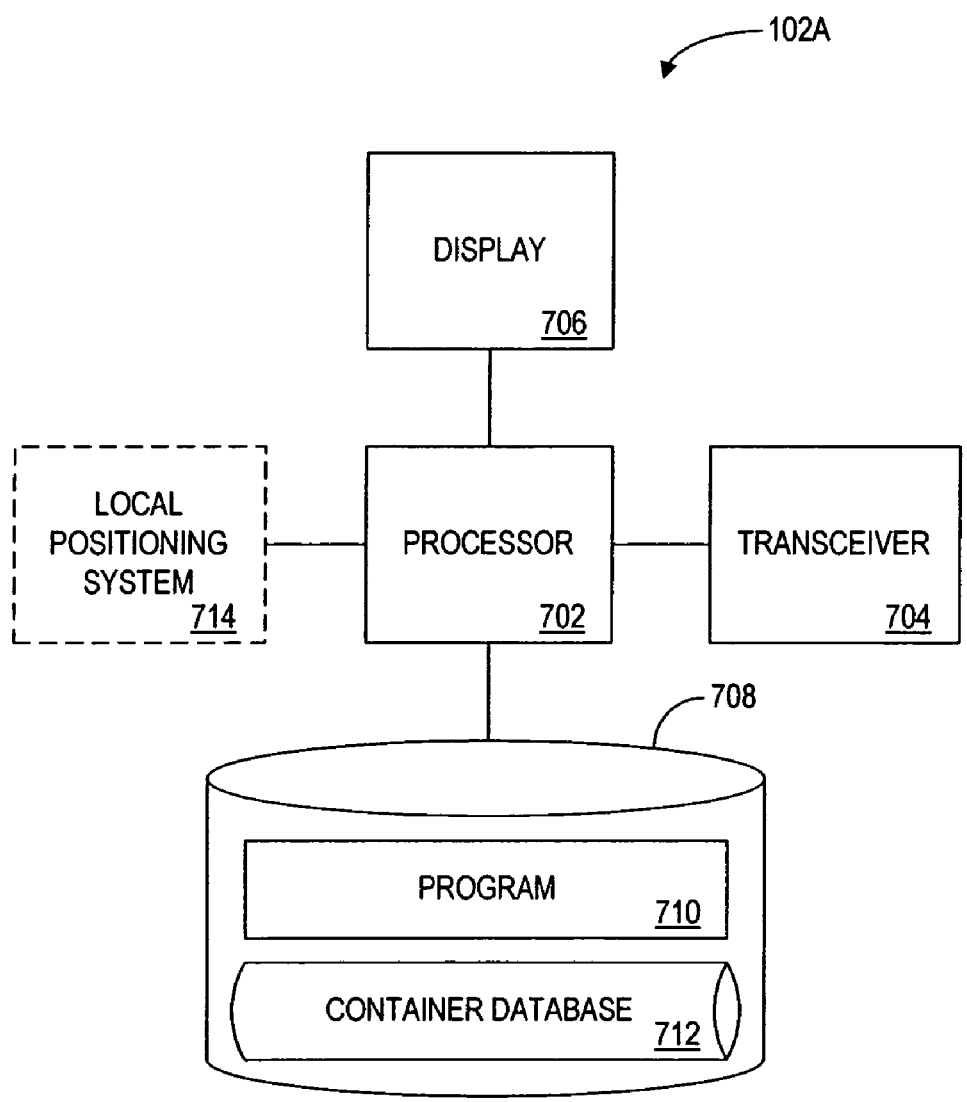
FIG. 7A is a schematic diagram of a first exemplary embodiment of a compliance monitoring device of the novel compliance system of FIG. 1B.

FIG. 7A is a schematic diagram of an exemplary embodiment of the compliance monitoring device 102 of FIG. 1B wherein the compliance monitoring device 102 is a medicine container 102a. For convenience, the exemplary embodiment of the compliance monitoring device 102 of FIG. 1B is referred to herein by reference numeral 102A in FIG. 7A; and only the relevant portions of the compliance monitoring device 102A (e.g., the portions of the compliance monitoring device 102A associated with increasing/monitoring compliance) are described herein. The compliance monitoring device 102A may be implemented as a system controller, as a dedicated hardware circuit, as an appropriately programmed general purpose computer, or as any other equivalent electronic, mechanical or electro-mechanical device.

The compliance monitoring device 102A comprises a processor 702, such as one or more conventional microprocessors (e.g., one or more Intel® Pentium® processors). The processor 702 is in communication with a transceiver 704 through which the processor 702 communicates with other devices (e.g., the controller 106, the medicine containers 110, 112 and 114, etc.). The processor 702 also is in communication with a display 706. The transceiver 704 may include multiple communication channels for simultaneous communication with the controller 106, and/or with the medicine containers 110, 112 and 114.

The processor 702 also is in communication with a data storage device 708. The data storage device 708 may comprise an appropriate combination of magnetic, optical and/or semiconductor memory, and may include, for example, Random Access Memory (RAM), Read-Only Memory (ROM), a compact disc and/or a hard disk. The processor 702 and the data storage device 708 each may be, for example, located entirely within a single computer or other computing device; or connected to each other by a communication medium, such as a serial port cable, a telephone line or a radio frequency transceiver. Alternatively, the compliance monitoring device 102A may comprise one or more computers that are connected to a remote server computer (not shown) for maintaining databases.

The data storage device 708 may store, for example, (i) a program 710 (e.g., computer program code and/or a computer program product) adapted to direct the processor 702 in accordance with the present invention, and particularly in accordance with the processes described in detail hereinafter with regard to the compliance monitoring device 102A; and (ii) a container database 712 adapted to store proximity information and compliance information regarding each medicine container employed within the novel compliance system 100 (e.g., the compliance monitoring device 102A/medicine container 102a and the medicine containers 110, 112 and 114 in FIG. 1B).

The program 710 may be stored in a compressed, in an uncompiled and/or in an encrypted format. The program 710 also may include program elements such as an operating system, a database management system and "device drivers" that allow the processor 702 to interface computer peripheral devices (e.g., a video display such as the display 706, a keyboard, a mouse, etc.).

Note that instructions of the program 710 may be read into a main memory (not shown) of the processor 702 from a computer-readable medium other than the data storage device 708, such as from a ROM or from a RAM. While execution of sequences of instructions in program 710 causes processor 702 to perform the process steps described herein, hard-wired circuitry may be used in place of, or in combination with, software instructions for implementation of the processes of the present invention. Thus, embodiments of the present invention are not limited to any specific combination of hardware and software.

The compliance monitoring device 102A (and/or the other medicine containers 110-114) also may be provided with a local positioning system 714 (shown in phantom), such as a global positioning system (GPS), that allows the compliance monitoring device 102A to track the distance or distances between each medicine container and/or to help the patient 104 locate one or more of the medicine containers as described further below. For example, each medicine container may track its own location using the local positioning system 714, and the tracked location information for each medicine container may then be synchronized (e.g., by the compliance monitoring device 102A or by controller 106) to determine when/if the medicine containers were separated.

The processor 702 also may be in communication with a clock (not shown) that supplies time and date information to the processor 702 and that may comprise, for example, a clock internal to the processor 702, a clock external to the processor 702 or a clock embodied within the program 710 (e.g., based on a system clock not shown).

Note that each of the medicine containers 110-114 may be similarly configured to the compliance monitoring device 102A of FIG. 7A (e.g., as a medicine container that is configured to operate both as a medicine container and as a compliance monitoring device). In this manner, any of the medicine containers 102a, 110, 112 and 114 may serve as a compliance monitoring device. Alternatively, the medicine containers 110-114 may include a subset of the components and/or of the features of the compliance monitoring device 102A of FIG. 7A. For example, each medicine container 110-114 may be provided with the processor 702, the transceiver 704, the display 706, the data storage device 708 and/or the local positioning system 714 for (1) monitoring whether a portion of a medicine stored within the medicine container was removed from the medicine container; (2) communicating with other medicine containers and/or with the compliance monitoring device 102A (e.g., for communicating when a portion of the medicine stored within the medicine container has been taken by the patient 104, for receiving reminders about when to take or not to take the medicine stored within the medicine container, etc.); (3) displaying warnings and/or reminders to the patient 104 regarding the taking of the medicine stored within the medicine container; and (4) tracking the location of the medicine container. U.S. Pat. No. 5,852,590 to de la Huerga, which is hereby incorporated by reference herein in its entirety, discloses methods of displaying messages on a cap of a container. These methods may be employed with the medicine containers of the present invention. Other functions also may be performed (described below). For example, each medicine container may be programmed with all of the information necessary for the medicine container to be "self-regulating" (e.g., by communicating with other medicine containers). That is, in at least one embodiment of the invention, each medicine container 102*a*, 110, 112 and 114 may communicate information to other medicine containers that indicates when medicine was removed from the medicine container, each medicine container may receive information that indicates when medicine was removed from other medicine containers, and each medicine container may determine, based on a schedule for taking medicines and/or based on incompatibility information about medicines stored within the medicine container's container database 712, whether a party should take a medicine stored within the medicine container. For "self-regulating" medicine containers, the controller 106 may track the patient 104's compliance to a medicine schedule merely by monitoring whether the medicine containers 102*a*, 110, 112 and 114 are being kept together.

Figure 7B:
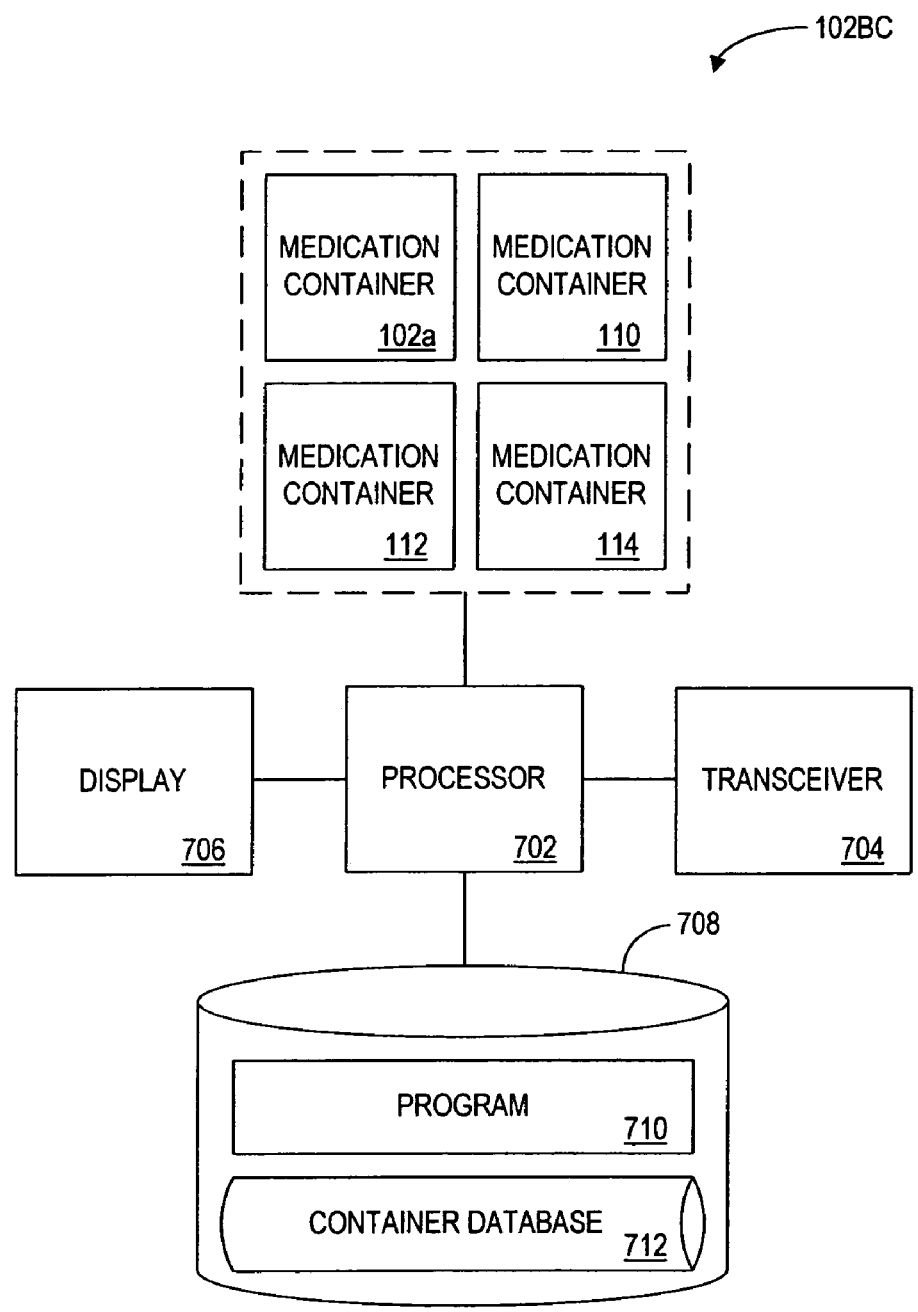
FIG. 7B is a schematic diagram of a second exemplary embodiment of a compliance monitoring device of the novel compliance system of FIGS. 1C-1D.

FIG. 7B is a schematic diagram of an exemplary embodiment of the compliance monitoring device 102 of FIGS. 1C-1D wherein the compliance monitoring device 102 is a central monitoring device (e.g., the meta-container 102*b* of FIG. 1C or the mini-container 102*c* of FIG. 1D)). For convenience, the exemplary embodiment of the compliance monitoring device 102 of FIGS. 1C-1D is referred to herein by reference number 102BC in FIG. 7B, and only the relevant portions of the compliance monitoring device 102BC are described herein.

With reference to FIG. 7B, the compliance monitoring device 102BC is in communication with the four medicine containers 102*a*, 110, 112 and 114. In at least one embodiment, the compliance monitoring device 102BC may communicate with any number (e.g., one, two, three or four) of the medicine containers as the medicine containers may communicate relevant information between one another (e.g., information such as when a medicine was removed from a medicine container, how much medicine was removed from the medicine container, etc.). The compliance monitoring device 102BC may communicate with one or more of the medicine containers 102*a*, 110, 112, and 114 via any communications mechanism (e.g., via a wireless channel, via an electrical or optical connection, etc.). In the embodiment of FIG. 7B, the compliance monitoring device 102BC is configured similarly to the compliance monitoring device 102A of FIG. 7A. That is, the compliance monitoring device 102BC of FIG. 7B includes the processor 702, the transceiver 704, the display 706, the data storage device 708, the program 710 and the container database 712. The compliance monitoring device 102BC of FIG. 7B therefore may communicate wirelessly with the medicine containers 102*a*, 110, 112 and 114 via the transceiver 704.

A sample of the contents of a container database record 712*a* of the container database 712 of FIGS. 7A and 7B is shown in FIG. 8. The specific data and fields illustrated in FIG. 8 represent only one embodiment of the records stored in the container database 712 of the invention. The data and fields of this database can be readily modified, for example, to include more or fewer data fields. A plurality of databases also may be employed to store the data and fields.

With reference to FIG. 8, the container database record 712*a* contains information related to a schedule for taking medicines, and various compliance/proximity information. Specifically, the container database record 712*a* contains, for example,: (1) a patient ID sub-record 802 that identifies the patient associated with the container database record 712*a* (e.g., patient ID P-123-45-6789 that identifies Jane Doe as shown in the patient database 210 of the controller 106 of FIG. 3); (2) a container ID sub-record 804 that identifies the medicine container associated with the container database record 712*a* (e.g., container ID: C-562-891 that identifies medicine container 102*a* (FIG. 1B)); (3) a prescription ID sub-record 806 that identifies the medicine stored within the medicine container identified by the container ID sub-record 804; (4) a prescription rules sub-record 808 that identifies a schedule for taking the medicine identified by the prescription ID sub-record 806 (e.g., one pill taken three times a day at six hour intervals); (5) a date/time sub-record 810 that identifies the time period covered by the container database record 712*a*; and (6) compliance sub-records 812-826 that identify compliance/proximity information regarding the taking of the medicine identified in the prescription ID sub-record 806 relative to the medicine in the other medicine containers (e.g., the medicine containers 110-114).

Each compliance sub-record 812-826 has fields corresponding to, for example, (1) a container ID 828 that identifies a medicine container for which compliance/proximity information is stored in the compliance sub-record; (2) a prescription ID 830 that identifies the medicine stored within the medicine container identified by the container ID 828 of the compliance sub-record; (3) rules 832 that identify conditions for taking the medicine identified by the prescription ID sub-record 806 relative to the taking of the medicine identified by the prescription ID 830 of the compliance sub-record (e.g., −2 hours indicates that the medicines cannot be taken within 2 hours of one another, +2 hours indicates that the medicines must be taken within 2 hours of one another, etc.); (4) a rules compliance indicator 834 that indicates a level of compliance to the rule 832 (e.g., 100%, 80%, 10%, etc.) of the compliance sub-record; (5) a proximity start time 836 that identifies a time when the medicine container identified in the container ID sub-record 804 and the medicine container identified by the container ID sub-record 828 of the compliance sub-record are sufficiently proximate to allow the two containers to wirelessly communicate; (6) a proximity end time 838 that identifies a time when the medicine container identified in the container ID sub-record 804 and the medicine container identified by the container ID sub-record 828 of the compliance sub-record are no longer sufficiently proximate to allow the two containers to wirelessly communicate; and (7) a proximity compliance indicator 840 that indicates a level of compliance by the patient identified in the patient ID sub-record 802 to a "proximity requirement" of the novel compliance system 100 (e.g., a pre-determined duration of time that medicine containers must be positioned sufficiently proximate to one another to allow wireless communications between the medicine containers, a predetermined duration of time beyond which medicine containers cannot be separated sufficiently so as not to wirelessly communicate, etc.). For example, assuming that the proximity requirement of the novel compliance system 100 is that medicine containers cannot be separated for more than 15 minutes, FIG. 8 illustrates that during the time period from 00:00 to 14:00, the container C-562-891 and the container C-152-906 were able to communicate for all but 5 minutes. Accordingly, the proximity compliance indicator 840 is 100% for this time period (e.g., as indicated by sub-records 812 and 814). However, from 14:00 to 14:30, the container C-562-891 and the container C-152-906 were unable to communicate (e.g., for 30 minutes) so that the proximity compliance indicator 840 is reduced for this time period (e.g., to 85% as indicated by sub-record 816).

Note that the rules 832 (and any proximity requirements of the novel compliance system 100) may be embodied within computer program code of the program 710 rather than being contained within the container database 712. Further, in embodiments wherein proximity information, rather than compliance information, is sent to the controller 106 (as described below), the compliance monitoring device 102 need not compute compliance data and the container database 712 need not store compliance rules and/or compliance information.

Other information which may be stored within the container database 712 or within any other database of the compliance monitoring device 102 of FIGS. 7A and 7B includes, for example:

(1) the identity of each medicine (e.g., the medicine's generic name, the medicine's brand name, an identifying code for the medicine, etc.);

(2) the name of the pharmaceutical company that manufactures each medicine;

(3) any other relevant prescription information (e.g., the time of day the medicine should be taken, the number of times a day the medicine should be taken, whether the medicine should be taken with food, the appropriate dose of the medicine to be taken, a time interval the patient should wait between doses, a duration of time the patient should take the medicine, etc.);

(4) the purpose of each medicine (e.g., to lower blood pressure, to thin the blood, to lower cholesterol, to reduce depression, etc.);

(5) interactions of each medicine with other medicines (e.g., other medicines that are part of a medicine schedule of the patient, whether the interactions are adverse or synergistic, etc.);

(6) the cost of each medicine; and (7) the amount of each medicine that was dispensed to the patient (e.g., the number of pills, the net weight of the dispensed medicine, etc.).

Exemplary Operations of the Novel Compliance System 100

Figure 9:
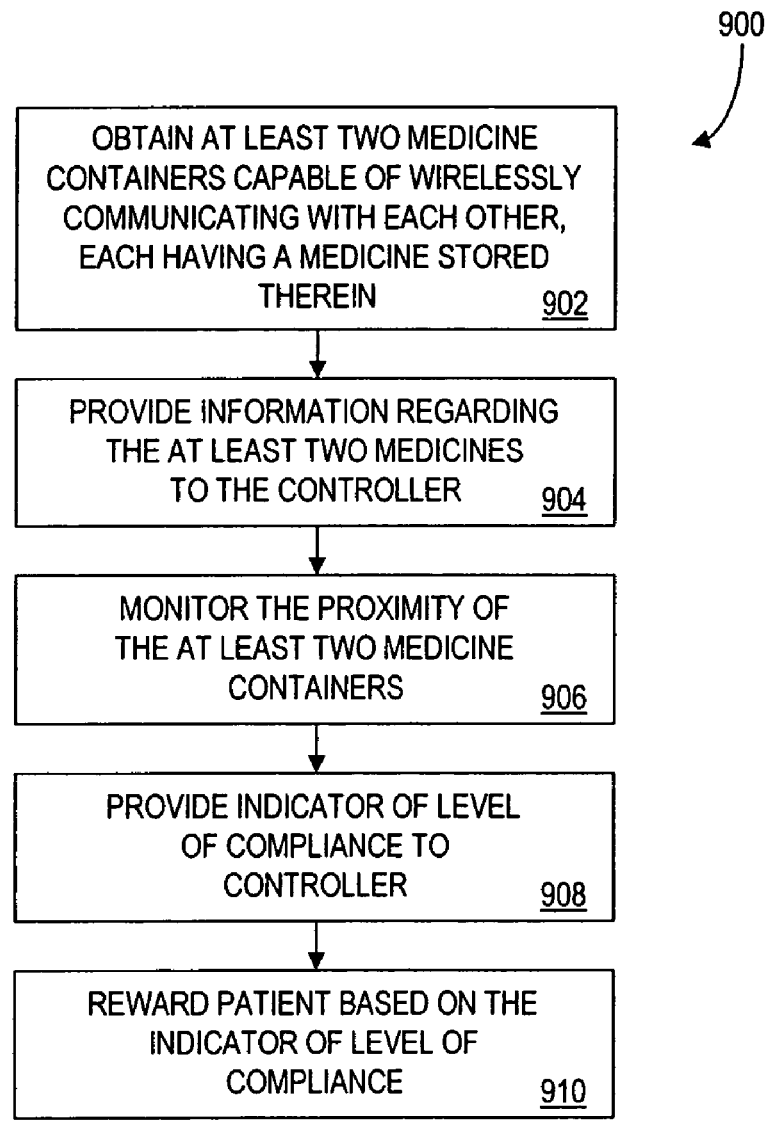
FIG. 9 is a flow chart of a first exemplary process of the novel compliance system of FIGS. 1A-8.

FIG. 9 is a flow chart of a first exemplary process 900 of the novel compliance system 100 of FIGS. 1A-8, useful in describing the general operation of the novel compliance system 100. The specific operations of the compliance monitoring device 102 and of the controller 106 are described below with reference to FIGS. 10-11 and FIGS. 12-13, respectively.

With reference to FIG. 9, the first exemplary process 900 begins in step 902 when the patient 104 obtains two or more medicine containers each of which: (1) is capable of wirelessly communicating with another medicine container; (2) stores a medicine; and (3) is programmed with information regarding the medicine stored within the medicine container (e.g., with any or all of the information in the container database 712 described previously with reference to FIGS. 7A-8 such as a patient ID, a container ID, a prescription ID, prescription rules, etc.). The medicine containers may comprise, for example, the medicine containers 102a, 110, 112 and 114 (FIGS. 1B-1D).

The patient 104 may obtain the medicine containers by purchasing the medicine containers (together with or separately from each medicine), or the medicine containers may be obtained for "free" with the medicines (e.g., from an insurance company, from a manufacturer of the medicines, from a physician, from a pharmacist, etc.). If the medicines are "prescribed" to the patient 104, a pharmacist, a physician or any other authorized person may provide each medicine container and/or each prescribed medicine to the patient 104. Non-prescription medicines may be similarly obtained and stored within one or more of the inventive medicine containers. If the novel compliance system 100 employs a central monitoring device (such as the meta-container 102b or the mini-container 102c as described previously with reference to FIG. 7B), an insurance company, a pharmacist, and/or a physician, may provide the patient 104 with the central monitoring device.

The medicine containers and/or the central monitoring device may be programmed by any known mechanism and by any party (e.g., by an insurance company, by a physician, by a pharmacist, by the patient, etc.). For example, the program 710 (FIG. 7A) of each medicine container may contain computer program code that directs the processor 702 to employ the transceiver 704 so as to receive information required to complete one or more container database records 712a for the medicine container and that directs the processor 702 to generate and store the one or more container database records 712a within the container database 712 of the medicine container. A central monitoring device may be similarly programmed (if employed). Any other mechanism may be used to program the medicine containers (and/or the central monitoring device) such as a keyboard, a keypad, a touch screen on the display 706, an infrared (IR) port, a bar code scanner, etc. Programmable labels similarly may be employed to store medicine information (see, for example, previously incorporated U.S. Pat. No. 5,852,590 to de la Huerga and U.S. Pat. No. 5,963,136 to O'Brien which is hereby incorporated by reference herein in its entirety).

After the medicine containers have been obtained, in step 904, information required by the controller 106 to monitor compliance of the patient 104 to a schedule for taking the medicines is provided to the controller 106. Exemplary information which may be provided to the controller 106 includes but is not limited to:

(1) the identity of each medicine (e.g., the medicine's generic name, the medicine's brand name, an identifying code for the medicine, etc.);

(2) the name of the pharmaceutical company that manufactures each medicine;

(3) the prescribed method for taking each medicine (e.g., the time of day the medicine should be taken, the number of times a day the medicine should be taken, whether the medicine should be taken with food, the appropriate dose of the medicine to be taken, a time interval the patient should wait between doses, a duration of time the patient should take the medicine, etc.);

(4) the purpose of each medicine (e.g., to lower blood pressure, to thin the blood, to lower cholesterol, to reduce depression, etc.);

(5) interactions of each medicine with other medicines (e.g., other medicines that are part of a medicine schedule of the patient, whether the interactions are adverse or synergistic, etc.);

(6) the cost of each medicine;

(7) the amount of each medicine that was dispensed to the patient (e.g., the number of pills, the net weight of the dispensed medicine, etc.);

(8) the identity of the patient, the identity of the prescribing party and/or the identity of the party filling the prescription;

(9) the medical history of the patient (e.g., so that patient specific warnings may be provided, including warnings that the patient is allergic to certain medicines, that the patient is pregnant and should not take one or more medicines, that the patient is a child and should not take an adult dose, etc.);

(10) the number of medicines that the patient has been prescribed (e.g., when each medicine container is programmed with all of the information necessary for the medicine container to be "self-regulating" by communicating with other medicine containers, to track compliance, an insurance company may need to track only that all the medicine containers are being kept together); and

(11) information regarding non-prescription medicines taken by the patient (e.g., as herbal remedies such as St. John's Wort may interact with prescription medicines, reduce the effectiveness of prescription medicines, and/or cause adverse reactions).

The above information may be provided to the controller 106 by any method. For example, if an insurance company employs the controller 106 and if the patient 104 is a member of the insurance company's compliance rewards program, the patient 104 may present a card to a pharmacist to notify the pharmacist that information regarding any prescription filled by the pharmacist should be sent to the insurance company. Alternatively, information regarding the medicines may be provided to the controller 106 by the patient 104 (e.g., the patient may submit a claim to the insurance company in order to receive payment for the prescribed medicines and the insurance company may obtain information regarding the medicines from the submitted claim).

Specific information about medicines also may be obtained by the controller 106 from various reference sources (e.g., from a WEB site, from a reference book, from a manufacturer's specification sheet, etc.). In an embodiment wherein the controller 106 is not operated by an insurance company (e.g., when the controller 106 forms part of an authentication server that may, for example, collect and authenticate compliance data and provide the authenticated compliance data to an insurance company), the controller 106 may receive information regarding the medicines from an insurance company.

The medicine containers may send information to the controller 106, as may a compliance monitoring device. For example, if a patient employs a meta-container 102b (FIG. 1C) with the medicine containers, the medicine containers may "log in" to the controller 106 (e.g., dial in to the controller 106) and relay information to the controller 106 when the medicine containers are placed in the meta-container 102b. In general, any mechanism and any medium may be employed to send the information to the controller 106 (e.g., a telephone connection, a radio link, a keypad, an Internet connection, a facsimile machine, etc.).

Once the controller 106 has received the above described information, in step 906 the compliance monitoring device 102 monitors the proximity of the two or more medicine containers (e.g., the compliance monitoring device 102 determines whether the at least two medicine containers are sufficiently proximate to wirelessly communicate). For example, the compliance monitoring device 102 may poll the medicine containers, the medicine containers may periodically transmit signals to the compliance monitoring device 102, etc.

In step 908, based on the monitored proximity information, the compliance monitoring device 102 provides (e.g., directly or via the patient 104) the controller 106 with at least an indicator of a level to which the patient 104 has complied with a schedule for taking the medicines stored within each medicine container (e.g., a "compliance indicator"). As will be described further below with reference to FIGS. 10-13, the compliance indicator that the compliance monitoring device 102 provides to the controller 106 may be, for example, (1) information regarding the proximity of the medicine containers (e.g., the times the medicine containers were separated and could not communicate, the times the medicine containers were together and could communicate, etc.); (2) one or more levels to which the patient 104 has complied with a proximity requirement for the medicine containers (e.g., a proximity requirement set by an insurance company, by the controller 106, by an authentication server, etc., such as a pre-determined, maximum time period that the medicine containers may be separated) as determined by the compliance monitoring device 102; (3) information regarding the medicines taken by the patient (e.g., the amount of each medicine taken by the patient 104, the time each medicine was taken by the patient, etc.); and/or (4) one or more levels to which the patient 104 has complied with one or more schedules for taking the medicines stored within the medicine containers (e.g., a level to which the patient 104 has complied with a schedule for taking each medicine, a level to which the patient 104 has complied with a schedule for taking multiple medicines, etc.) as determined by the compliance monitoring device 102.

Note that the specific compliance indicator provided by the compliance monitoring device 102 to the controller 106 may affect the information that is stored by the compliance monitoring device 102 and/or by the controller 106. For example, if the compliance monitoring device 102 merely provides the controller 106 with information regarding the proximity of the medicine containers, the container database 712 of the compliance monitoring device 102 need not store information such as compliance requirements (e.g., sub-record 832), compliance levels (e.g., sub-records 834 and 840), etc. However, if the compliance monitoring device 102 provides the controller 106 with one or more levels to which the patient 104 has complied with a schedule for taking medicines, the compliance monitoring device 102 need not send to the controller 106 much of the compliance information described previously with reference to step 904 (e.g., as the controller 106 need not compute a level of compliance). Compliance levels (and exemplary methods for determining compliance levels) are described below with reference to FIG. 10.

In step 912, the controller 106 rewards the patient 104 based on the indicator of the level (or levels) of compliance provided by the compliance monitoring device 102. For example, in exchange for complying with a medicine schedule or for complying with any proximity requirements for the medicine containers, the patient 104 may receive lower insurance premiums, reduced insurance premiums or co-payments, etc., as described below with reference to FIGS. 12-13. Note that depending on the exact compliance indicator provided to the controller 106, the controller 106 may be required to compute one or more compliance levels based on the compliance indicator (e.g., based on proximity information, based on the times the patient 104 took one or more medicines, etc.) before rewarding the patient 104 (as described below).

First Exemplary Operation of the Compliance Monitoring Device 102

Figure 10:
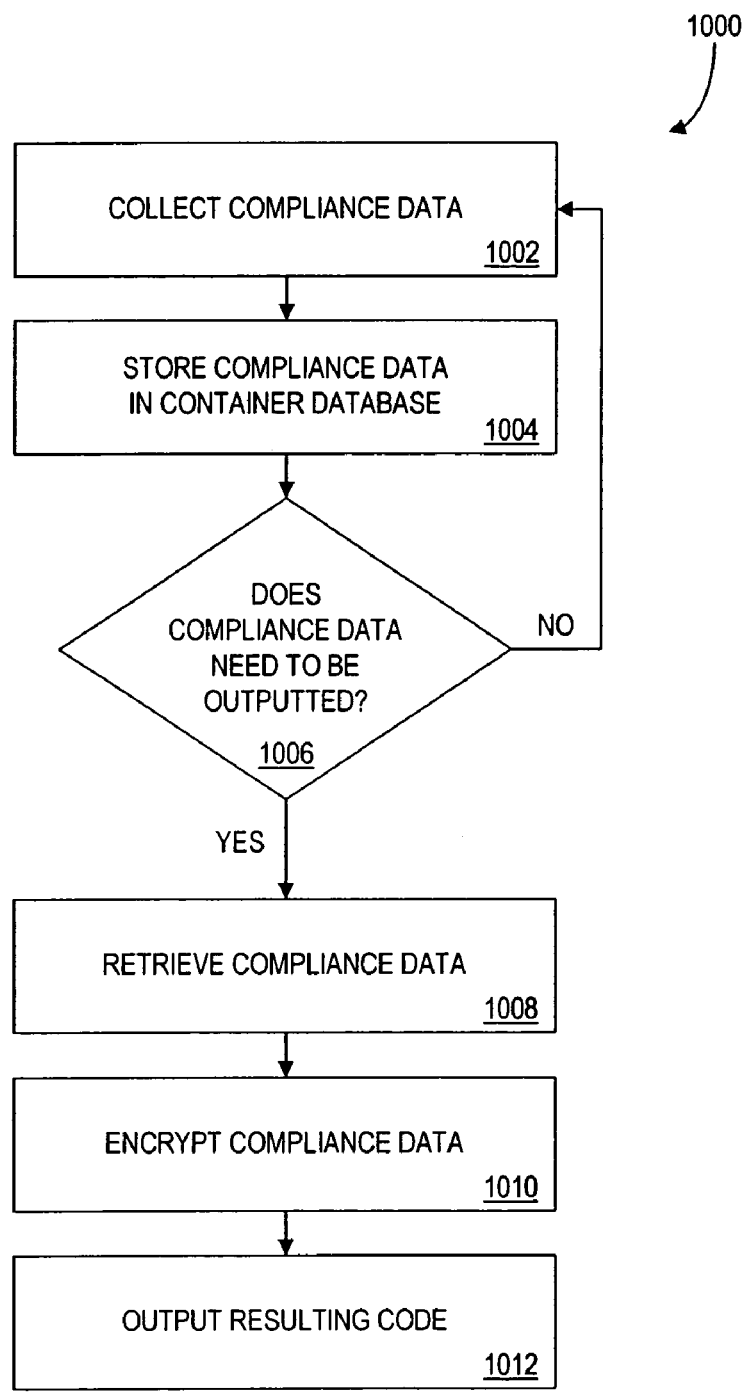
FIG. 10 is a flow chart of a first exemplary process by which a compliance monitoring device of the novel compliance system of FIGS. 1A-8 monitors and tracks the compliance of a patient to a schedule for taking medicines.

FIG. 10 is a flow chart of a first exemplary process 1000 by which the compliance monitoring device 102 may monitor and track the compliance of the patient 104 to a schedule for taking medicines. The process 1000 and the other processes described below with reference to the compliance monitoring device 102 may be embodied within computer program code of the program 710 of the data storage device 708 and may each comprise a computer program product. The process 1000 is described with reference to FIGS. 1B-1D wherein the patient 104 is required to comply with a schedule for taking four medicines stored within the medicine containers 102a, 110, 112 and 114. It will be understood that the same process may be employed whether the compliance monitoring device 102 is merely a central monitoring device (e.g., a meta-container 102b (FIG. 1C) or a mini-container 102c (FIG. 1D)) or a medicine container (e.g., the medicine container 102a of FIG. 1B).

With reference to FIGS. 1B-1D and 10, the process 1000 begins in step 1002 when the compliance monitoring device 102 collects data regarding the patient 104's compliance with a schedule for taking the medicines stored within the medicine containers 102a, 110, 112 and 114 (e.g., the compliance monitoring device collects "compliance data"). Specifically, the compliance monitoring device 102: (1) determines proximity information regarding the medicine containers 102a, 110, 112 and 114; and (2) determines a level of compliance to the medicine schedule based at least in part on the determined proximity information.

As stated previously with reference to FIGS. 7A and 7B, one type of proximity information that may be obtained by the compliance monitoring device 102 is whether each medicine container 102a, 110, 112 or 114 has been moved beyond a range wherein the medicine container may communicate with the other medicine containers (e.g., whether, for a pre-determined amount of time, any of the medicine containers 102a, 110, 112 or 114 have been unable to wirelessly communicate). The proximity information obtained by the compliance monitoring device 102 alternatively, or additionally, may comprise, for example, (1) the times each medicine container has been moved beyond a range wherein the medicine container may communicate with the other medicine containers and/or with the compliance monitoring device 102; (2) the number of times each medicine container has been moved beyond a range wherein the medicine container may communicate with the other medicine containers and/or with the compliance monitoring device 102; and/or (3) the distance (or the change in the distance) between the medicine containers and/or the compliance monitoring device 102 (e.g., as determined by the local positioning system 714 of each medicine container, by the strength of signals transmitted between the medicine containers and/or the compliance monitoring device 102, or by any other position (or relative position) determination mechanism).

Once the compliance monitoring device 102 obtains proximity information regarding the medicine containers 102a, 110, 112 and 114, the compliance monitoring device 102 determines a level of compliance to the medicine schedule based at least in part on the proximity information. One method for determining a level of compliance is to identify (based on the proximity information) whether, for a pre-determined time period, any of the medicine containers 102a, 110, 112 or 114 were unable to wirelessly communicate with one another (e.g., whether any of the medicine containers were "out of range" of one another). If any of the medicine containers were out of range of one another for longer than a pre-determined time period (e.g., 15 minutes, 10 minutes, 5 minutes, etc.), the patient 104's compliance level may be reduced from 100% as previously described with reference to FIG. 8. Alternatively, or additionally, an indication that the medicine containers were out of range of one another for longer than a predetermined time period may be stored (e.g., within the container database 712 of the compliance monitoring device 102).

The predetermined time period may be fixed (e.g., may be the same time period for each medicine container) or may vary (e.g., may be different for one or more of the medicine containers). For example, a predetermined time period of 20 minutes may be assigned to a medicine container that contains a powdered medicine that must be dissolved in water and then consumed, while a pre-determined time period of 10 minutes may be assigned to a medicine container that contains a chewable medicine. A "refill" exception may be provided wherein proximity information is not collected or is ignored, or wherein the patient 104 or some other party may notify the insurance company when a medicine container is being refilled (e.g., at a pharmacy). In this manner, the patient 104 is not penalized when one or more medicine containers are separated for a legitimate reason.

Note that while a medicine container being out of range of one or more other medicine containers and/or of the compliance monitoring device 102 for longer than a pre-determined time period may be an indicator that the patient 104 has not complied with a medicine schedule, a medicine container being out of range of one or more other medicine containers also may indicate that the patient 104 is taking a medicine stored in the out of range medicine container (e.g., depending on the communication range of the medicine containers). Accordingly, the failure of the patient 104 to move a medicine container beyond the range of the other medicine containers (and/or the compliance monitoring device 102) may indicate that the patient 104 has not taken the medicine stored within the medicine container and may constitute a failure of the patient 104 to comply with the medicine schedule (e.g., the compliance monitoring device 102 may deem the patient to be in non-compliance of the medicine schedule).

In addition to determining compliance data based on proximity information, the compliance monitoring device 102 may determine compliance data based on other measures of the patient 104's compliance to the medicine schedule. For example, the compliance monitoring device 102 may monitor (1) the amount of each medicine that has been taken by the patient 104; (2) the timing of the taking of each medicine; (3) various physical indications of the patient 104 (e.g., the patient 104's blood pressure, the patient 104's heart rate, the patient 104's blood glucose level, etc.) that may indicate whether or not the patient 104 has taken one or more medicines; and/or (4) any attribute that indicates the patient 104 has complied with a medicine schedule. For example, a pressure sensor may be employed within the cap of each medicine container 102a, 110, 112 and 114 that identifies each time the cap is opened or closed (as described, for example, in previously incorporated U.S. patent application Ser. No. 09/165,089, filed Oct. 1, 1998, which is now U.S. Pat. No. 6,751,730 B1), and opened/ closed information may be transmitted to the compliance monitoring device 102 or to one or more of the medicine containers. A weight sensor may be employed within the base of each medicine container 102a, 110, 112 and 114 that identifies the weight of the medicine stored within the medicine container, and weight information may be transmitted to the compliance monitoring device 102 or to one or more of the medicine containers. Other suitable weight sensors are described in U.S. Pat. No. 5,014,798 to Glynn which is hereby incorporated by reference herein in its entirety. A radio-frequency identifier (RFID) may be embedded within each medicine (e.g., in each pill), and each medicine container and/or the compliance monitoring device 102 may be provided with an RF scanner that senses the RFIDs so as to identify when medicine is removed from a medicine container (e.g., so as to count the number of pills taken by the patient 104). After obtaining information regarding the amount of medicine taken by the patient 104 (by employing one or more of the above-described techniques), the compliance monitoring device 102 may determine a level of compliance to the medicine schedule. The compliance monitoring device 102 may determine a first compliance level based on proximity information (e.g., proximity information about the medicine containers 102a, 110, 112 and 114) and may determine a second compliance level based on medicine consumption information (e.g., the amount of medicine taken by the patient 104). Alternatively, or additionally, the compliance monitoring device 102 may determine a single, "composite" compliance level based on both proximity information and medicine consumption information.

In addition to tracking the number of pills dispensed from each medicine container, the compliance monitoring device 102 also may track the times/intervals at which the pills were dispensed. The number of pills and the times/intervals at which the pills were dispensed may be stored (e.g., pill 1 was dispensed at 9:00 a.m., pill 2 was dispensed 1 hour after pill 1, pill 3 was dispensed 1 hour after pill 2, etc.). Alternatively, the compliance monitoring device 102 may compare the number of pills and the times/intervals at which the pills were dispensed with a stored, prescribed schedule of taking the pills (e.g., a schedule that states "take one pill at a time at one hour intervals"), and the compliance monitoring device 102 may store an indication that the first three pills were taken in compliance with the prescribed schedule (e.g., by storing an indicator within a register (not shown)).

After determining the compliance data, in step 1004, the compliance monitoring device 102 stores the compliance data (e.g., within one or more records of the container database 712 as described previously with reference to FIG. 8). Note that in at least one embodiment of the invention, the compliance data need not be stored by the compliance monitoring device 102, and may be output as described below with reference to step 1012 or encrypted and output as described below with reference to steps 1010 and 1012.

In step 1006, the compliance monitoring device 102 determines if the compliance data needs to be output. For example, to allow the patient 104 to qualify for a compliance rewards program, an insurance company that employs the controller 106 may require that the patient 104 communicate the compliance data to the insurance company on a periodic basis (e.g., daily, weekly, monthly, etc.), after completing all or part of a medicine regime, or after some other demarcation. Accordingly, the compliance monitoring device 102 may be programmed to automatically output compliance data (as described below with reference to steps 1008, 1010 and 1012) or may output compliance data in response to an action of the patient 104 (e.g., the pressing of a button 118 as shown in FIG. 1B). If the compliance monitoring device 102 determines that the compliance data needs to be output (e.g., because of a schedule built into the program 710, because the patient 104 presses the button 118, because one or more of the medicine containers 102a, 110, 112 and 114 needs to be refilled, etc.), the process 1000 proceeds to step 1008; otherwise, the process 1000 returns to step 1002 to collect additional compliance data.

In step 1008, the compliance monitoring device 102 retrieves the compliance data (e.g., one or more compliance levels) previously stored by the compliance monitoring device 102. For example, the compliance monitoring device 102 may retrieve the rules compliance data 834, the proximity compliance data 840 and/or a combination thereof from the container database 712 (FIG. 8). Thereafter, in step 1010, the compliance monitoring device 102 encrypts the compliance data so as to generate "a code" (e.g., one or more symbols that represent the compliance data). The compliance data may be encrypted using any known encryption algorithm (e.g., using a one-way hash function or using any other encryption algorithm such as those described in Schneier, *Applied Cryptography 2$^{nd}$ Edition: protocols, algorithms, and source code in C*, John Wiley & Sons, Inc. (1996).), and the resulting code may have a predetermined length, a set length or an undetermined length. The compliance data that is encrypted may be the stored compliance data (described above) or may be compliance data calculated from the stored compliance data. For example, the compliance monitoring device 102 may merely store proximity information and/or information regarding how much of each medicine has been taken by the patient 104, without calculating one or more compliance levels. Thereafter, in response to a trigger (e.g., the patient 104 pressing the button 118, one or more of the medicine containers 102a, 110, 112 or 114 running out of medicine, etc.) or automatically (e.g., periodically such as every night, every week, etc.), the compliance monitoring device 102 may calculate one or more compliance levels (e.g., a proximity compliance level, a compliance level for the amount of each medicine taken by the patient 104, etc.) based on the stored compliance data. Each compliance level may be based, for example, on an evaluation of the stored compliance data, and may be normalized to a compliance level scale (e.g., 1 to 100). Each compliance level may then be encrypted.

In step 1012, the compliance monitoring device 102 outputs the encrypted code. The code may be output to the patient 104 (e.g., via a display 120 as shown in FIG. 1B), or may be output directly to the controller 106. For example, the compliance monitoring device 102 may display the code to the patient 104, and the patient 104 may provide the controller 106 with the code during a telephone call (e.g., via a plain-old-telephone service (POTS) line, via a cellular network, via an Internet telephone call, etc.), via standard or electronic mail or via the Internet. The patient 104 may send an image of the code (electronically, via standard mail, via facsimile, etc.) to the controller 106 (or to an insurance company that operates the controller 106). The image of the code may be generated via conventional photography (e.g., and sent through standard mail or scanned into a computer and sent electronically) or may be generated via digital photography (e.g., and sent electronically). The patient 104 also may capture the image on a networked video camera and may send the captured image electronically. Likewise, the patient 104 may call (e.g., via a telephone, via a cellular telephone, via an Internet telephone, etc.) the controller 106 (or an insurance company that employs the controller 106)

and may then press the button 118 on the compliance monitoring device 102 so that the compliance monitoring device 102 emits a series of tones (e.g., dual tone multiple frequency (DTMF) signals) during the call that communicate the code to the controller 106 (and/or to the insurance company). The communication of the code to the controller 106 may occur periodically, or at certain pre-determined times such as when a medicine container needs to be refilled, or at the end of a prescribed medicine regime. The patient 104 may call the controller 106 (or the insurance company) and communicate the code at an arbitrary time if desired.

The patient 104 alternatively, or additionally, may communicate the code to a doctor or to some other medical personnel (e.g., to a nurse, to an intern, etc.) who can in turn communicate the code (or the underlying compliance data) to controller 106 (and/or to the insurance company). In this manner, a doctor may monitor the patient 104's compliance, may determine, for example, if any symptoms experienced by the patient 104 are a result of non-compliance and otherwise may act accordingly (e.g., notify the insurance company, revise the patient 104's medicine schedule, schedule a doctor's visit, etc.).

The compliance monitoring device 102 (or any of the medicine containers 102*a*, 110, 112 and 114) may have a direct connection to the controller 106 (and/or to the insurance company) and may communicate the code via the direct connection (e.g., the controller 106 may query the compliance monitoring device 102 for the code, a networked video camera may capture an image of the code on the display 120 and transmit the image of the code to the controller 106, etc.). In some embodiments, the compliance monitoring device 102 may only encrypt compliance data and/or output a code that represents encrypted compliance data if one or more compliance levels are satisfied by the patient 104.

Numerous alternative operations may be performed during the process 1000. For example, each medicine container, rather than the compliance monitoring device 102, may output a different code that corresponds to compliance data associated with the medicine stored within the medicine container; or each medicine container may output the same code that corresponds to combined compliance data for all of the medicines stored within the medicine containers 102*a*, 110, 112 and 114. When the compliance monitoring device 102 is a medicine container (such as the medicine container 102*a* of FIG. 1B), only the medicine container that communicates within the controller 106 (e.g., the "head" medicine container) need output a code (e.g., the head medicine container may output a different code for each medicine container that corresponds to compliance data associated with the medicine stored within the medicine container; or the head container may output a single code that corresponds to combined compliance data for all of the medicines stored within the medicine containers 102*a*, 110, 112 and 114). A central monitoring device similarly may output a different code for each medicine container that corresponds to compliance data associated with the medicine stored within the medicine container, or may output a single code that corresponds to combined compliance data for all of the medicines stored within the medicine containers 102*a*, 110, 112 and 114.

As described previously with reference to FIGS. 1C-1D and FIG. 7B, rather than (or in addition to) communicating with each other, the medicine containers 102*a*, 110, 112 and 114 may communicate with a central monitoring device such as the meta-container 102*b* or the mini-container 102*c*. Alternatively, the central monitoring device may comprise a pager-like device, a personal digital assistant (PDA), a laptop computer, a desktop computer, etc. When a central monitoring device is employed, the proximity requirement for the medicine containers may be that all of the medicine containers remain proximate the central monitoring device (e.g., within a range that allows the medicine containers to communicate with the central monitoring device). The central monitoring device may then track when or if the medicine containers have been taken out of range of the central monitoring device. For example, each medicine container may have attached thereto an infrared (IR) or radio frequency (RF) tag (as is known in the art) that contains information that identifies the medicine stored within the medicine container. Alternatively, the patient 104 may be provided with tags to attach to the medicine containers (e.g., tags provided by a physician, a pharmacist, a manufacturer of the medicines and/or an insurance company). The patient 104 also may be provided with an IR scanner or with an RF scanner that can read the IR/RF tags when the tags are within range of the scanner. When a portable central monitoring device is employed (e.g., the mini-container 102C of FIG. 1D) the patient 104 may be able to separate (without being penalized) one or more medicine containers from the remainder of the patient's medicine containers (e.g., if the patient needs to take some but not all of the patient's medicines to work). The mini-container 102*c* may be programmed with the identity of the medicines that the patient needs throughout the day (e.g., all or a subset of the medicines stored within the medicine containers 102*a*, 110, 112 and 114), and in at least one embodiment, the mini-container 102*c* can download prescription information and prescription compliance information from a main central monitoring device (e.g., from the meta-container 102*b* of FIG. 1B).

As an example of the mini-container 102*c*'s operation, with reference to FIGS. 1D and 8, assume the patient 104 is required to take both medicines "R-102-365" (stored in medicine container 102*a*) and medicine "R-198-342" (stored in medicine container 114), but that the medicine "R-198-342" and the medicine "R-102-365" cannot be taken within 2 hours of one another. If the patient 104 takes medicine "R-102-365" at 7:00 a.m. (just before leaving home for work), the patient 104 will need to take medicine "R-198-342" while the patient is at work. Accordingly, the patient 104 places the medicine container 114 (which stores the medicine "R-198-342"), along with any other medicine containers having medicines that the patient 104 will take while at work, into the mini-container 102*c*. The mini-container 102*c* and the meta-container 102*b* (FIG. 1C) then communicate (e.g., wirelessly, via a cable, etc.) so as to transfer at least an indicator to the mini-container 102*c* that the patient 104 took medicine "R-102-365" at 7:00 a.m. Thereafter, the patient 104 separates the mini-container 102*c* from the meta-container 102*b*, and takes the mini-container 102*c* to work. If the patient 104 attempts to take the medicine "R-198-342" at 8:00 a.m., the mini-container 102*c* may issue a warning to the patient 104 that notifies the patient 104 that the medicine "R-198-342" should not be taken until at least 9:00 a.m. (e.g., at least 2 hours after the medicine "R-102-365" was taken). The medicine container 114 also may be programmed so as not to open until after 9:00 a.m.

The mini-container 102*c* also may record when the patient 104 takes the medicine "R-198-342", how much of the medicine "R-198-342" the patient 104 takes, etc., and may report this information to the meta-container 102*b* and to the mini-container 102c when the meta-container 102b and the mini-container 102c are positioned proximate one another.

Second Exemplary Operation of the Compliance Monitoring Device 102

Figure 11:
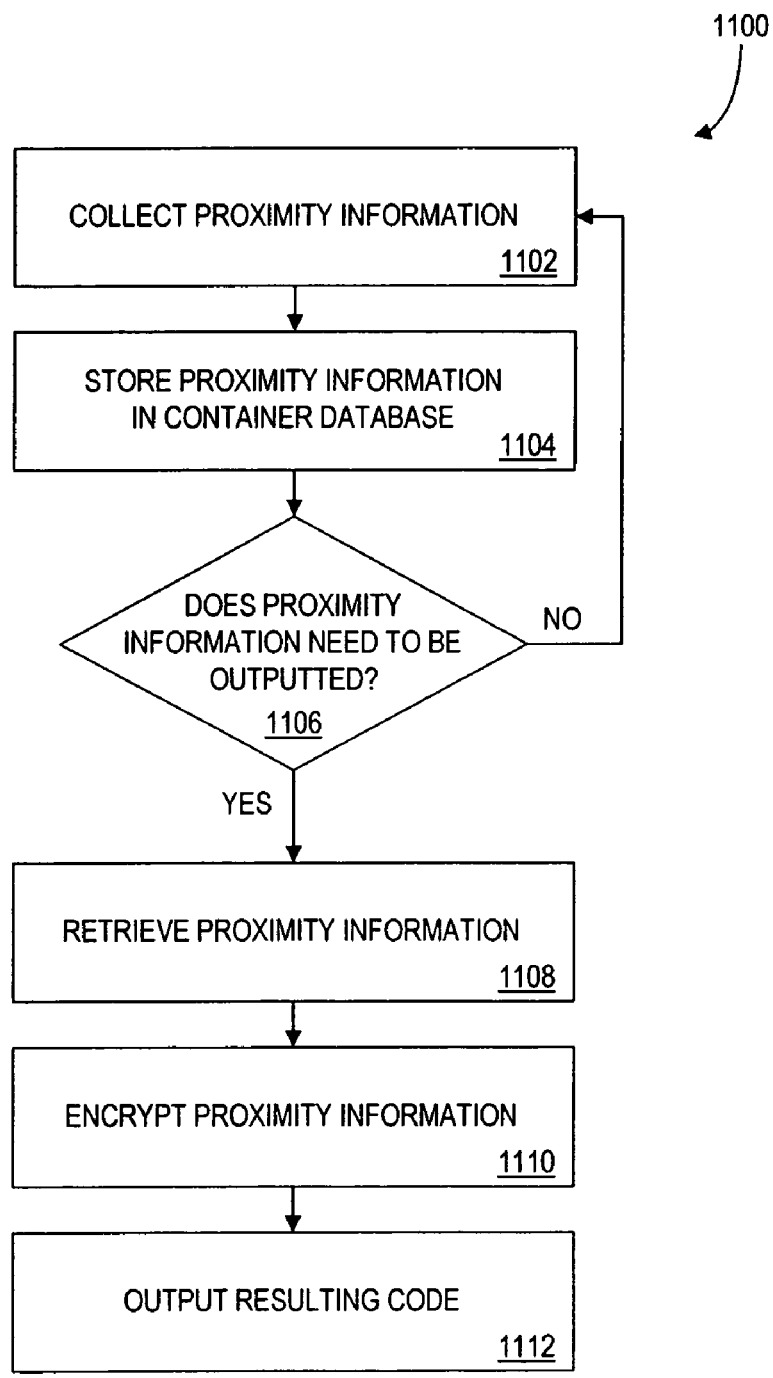
FIG. 11 is a flow chart of a second exemplary process by which a compliance monitoring device of the novel compliance system of FIGS. 1A-8 monitors and tracks the compliance of a patient to a schedule for taking medicines.

FIG. 11 is a flow chart of a second exemplary process 1100 by which the compliance monitoring device 102 may monitor and track the compliance of the patient 104 to a schedule for taking medicines. The second exemplary process 1100 of FIG. 11 is similar to the first exemplary process 1000 of FIG. 10. However, rather than storing and outputting compliance data (as is performed during the first exemplary process 1000), during the second exemplary process 1100, the compliance monitoring device 102 stores and outputs only proximity information (e.g., information regarding the proximity of the medicine containers 102a, 110, 112 and 114).

With reference to FIG. 11, the second exemplary process 1100 begins in step 1102 when the compliance monitoring device 102 collects information regarding the proximity of the medicine containers 102a, 110, 112 and 114 (as previously described with reference to process 1000 and step 1002). Once the compliance monitoring device 102 obtains proximity information regarding the medicine containers 102a, 110, 112 and 114, in step 1104 the compliance monitoring device 102 stores the proximity information (e.g., within one or more records of the container database 712 as described previously with reference to FIG. 8). Note that in at least one embodiment of the invention, the proximity information need not be stored, and may be output as described below with reference to step 1112, or encrypted and output as described below with reference to steps 1110 and 1112.

In step 1106, the compliance monitoring device 102 determines if the proximity information needs to be output. For example, an insurance company that employs the controller 106 may require that the patient 104 communicate the proximity information to the insurance company on a periodic basis (e.g., daily, weekly, monthly, etc.), after completing all or part of a medicine regime, or after some other demarcation. Accordingly, the compliance monitoring device 102 may be programmed to automatically output proximity information (as described below with reference to steps 1108, 1110 and 1112) or may output proximity information in response to an action of the patient 104 (e.g., the pressing of the button 118 as shown in FIG. 1B). If the compliance monitoring device 102 determines that the proximity information needs to be output (e.g., because of a schedule built into the program 710, because the patient 104 presses the button 118, because one or more of the medicine containers 102a, 110, 112 and 114 needs to be refilled, because of any of the reasons described previously with reference to process 1000 and FIG. 10, etc.), the process 1100 proceeds to step 1108; otherwise, the process 1100 returns to step 1102 to collect additional proximity information.

In step 1108, the compliance monitoring device 102 retrieves the proximity information previously stored by the compliance monitoring device 102. For example, the compliance monitoring device 102 may retrieve information regarding the times/duration each medicine container was out of range of the other medicine containers and/or the compliance monitoring device 102, the distance (or change in distance) between the medicine containers during a specific time period, etc. Thereafter, in step 1110, the compliance monitoring device 102 encrypts the proximity information so as to generate a code. The proximity information may be encrypted using any known encryption algorithm (e.g., a one-way hash function, etc.), and the resulting code may have a predetermined length, a set length or an undetermined length. The proximity information that is encrypted may be the stored proximity information (described above) or may be proximity information calculated from the stored proximity information (e.g., a calculated change in distance between medicine containers).

In step 1112, the compliance monitoring device 102 outputs the encrypted code. The code may be output to the patient 104 (e.g., via the display 120 as shown in FIG. 1B), or may be output directly to the controller 106.

First Exemplary Operation of the Controller 106

Figure 12:
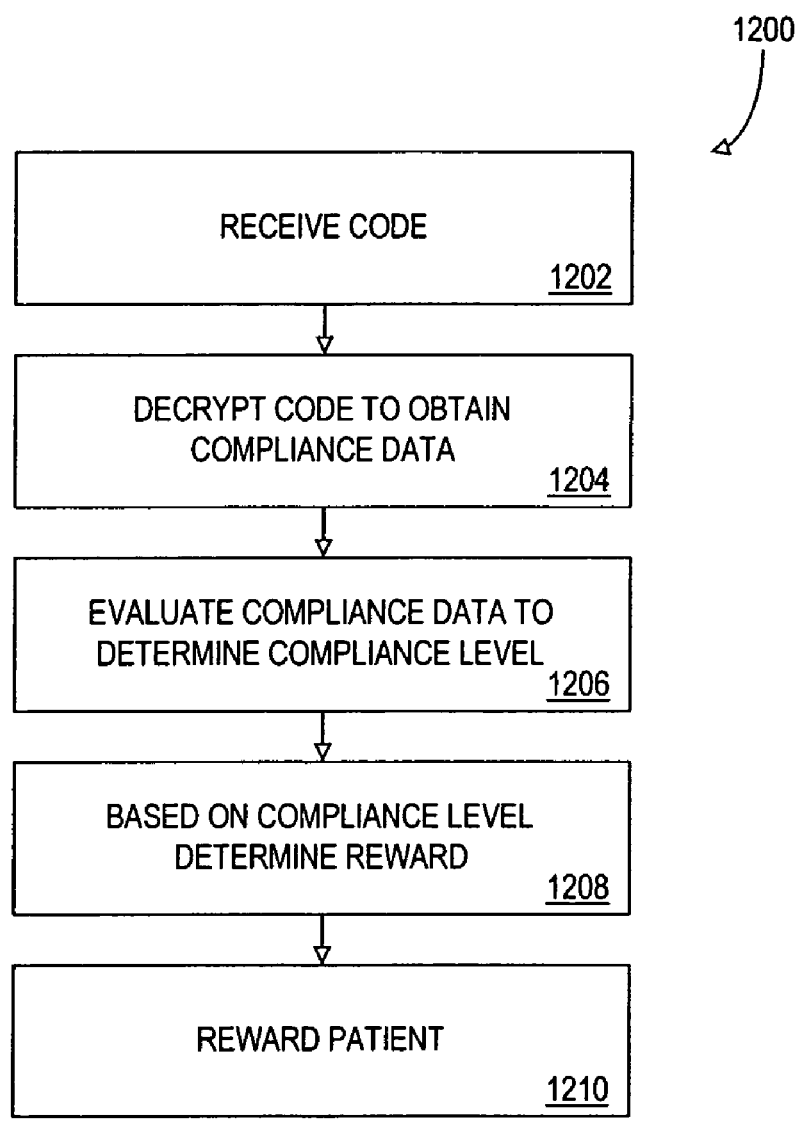
FIG. 12 is a flow chart of a first exemplary process by which a controller of the novel compliance system of FIGS. 1A-8 receives compliance data from a patient and rewards the patient based on the received compliance data.

FIG. 12 is a flow chart of a first exemplary process 1200 by which the controller 106 receives compliance data from the patient 104 (or from the compliance monitoring device 102) and rewards the patient 104 based on the received information. The process 1200 and the other processes described below with reference to the controller 106 may be embodied within computer program code of the program 208 of the data storage device 206 and each may comprise a computer program product.

With reference to FIG. 12, the process 1200 begins in step 1202 when the controller 106 receives a code that represents compliance data collected by the compliance monitoring device 102. In at least one embodiment of the invention, the code is sent to the controller 106 from the patient 104 or from the compliance monitoring device 102 (in step 1012 of process 1000 of FIG. 10). In general the code may be received from any party and/or from any device. For example, the code may be sent from a party that prescribed one or more of the medicines stored within the medicine containers 102a, 110, 112 and 114, from a party that filled one or more of the prescriptions for the medicines stored within the medicine containers 102a, 110, 112 and 114, from a family member, etc. Likewise, a telephone, a personal computer, a PDA, a medicine container, a meta-container (e.g., the meta-container 102b of FIG. 1C), a mini-container (e.g., the mini-container 102c of FIG. 1D), any other device associated with one or more of the medicine containers, etc., may send the code to the controller 106 via any communications medium (e.g., via a telephone network, via the Internet, via a wireless network, via a local area network, via a wide area network, via an intranet, via an extranet, via standard mail, via verbal communication, etc.). A central authentication server (e.g., another controller that authenticates compliance information) also may send the code to the controller 106.

In step 1204, the controller 106 decrypts the received code to determine the compliance data collected by the compliance monitoring device 102. The code may be decrypted by employing a decryption algorithm to recover the pre-encryption compliance data, or if the code was encrypted using a one-way function (e.g., a one-way hash function), rather than decrypting the code, the controller 106 may compare the received code with at least one code corresponding to an acceptable level of compliance. As described previously with reference to FIG. 10, the compliance data output by the compliance monitoring device 102 (step 1012) comprises one or more levels of compliance of the patient 104 (e.g., a level of compliance to a proximity requirement imposed by an insurance company, a level of compliance to a schedule for taking multiple medicines, a level of compliance to a schedule for taking one medicine, a composite level of compliance, etc.). The code received by the controller 106 alternatively (or additionally) may indicate proximity information or other compliance information that may be employed by the controller 106 to compute a compliance level (as described below with reference to FIG. 13).

In step 1206, the controller 106 evaluates the decrypted compliance data to determine at least one level of compliance of the patient 104 to a medicine schedule. As stated, the decrypted compliance data may already comprise one or more compliance levels so that the controller 106 need merely examine the decrypted code to determine the compliance level (or levels). Alternatively, the decrypted code may represent a first compliance level based on proximity information regarding the medicine containers 102a, 110, 112 and 114 and a second compliance level based on the amount of medicine taken by the patient 104. The decrypted code also may represent a single, "composite" compliance level based on both proximity information and medicine consumption information. Likewise, the code may provide any of the proximity and/or compliance information described previously with reference to the processes 1000 and 1100 of FIGS. 10 and 11.

Each compliance level used by the controller 106 (and/or by the) compliance monitoring device 102 may be based on a gradated compliance scale (e.g., a scale from 1 to 10). Alternatively, each compliance level may be an indication that a patient is not compliant, somewhat compliant, compliant, very compliant, extremely compliant, 86% compliant, etc. A compliance level also may be nothing more than an indication that a patient is "compliant" and "not compliant". Additionally, a "strike" system may be employed for determining each compliance level. For example, the patient 104 may be able to accumulate three "strikes" (e.g., three instances of non-compliance) before being considered to be "not compliant" or before the patient 104's compliance level drops by any amount (e.g., drops by 10%). If the patient 104 is responsible for communicating the code to the controller 106 (e.g., as shown in FIGS. 1B-1D), then whether the patient 104 communicates the code as required (e.g., as the patient 104 may be required to communicate the code before a certain time, periodically, etc.) may have a bearing on the patient's compliance level. A compliance level may be determined based on a number of times a cap of a medicine container was opened or closed within a pre-determined time period (e.g., as this data may indicate a number of times medicine within the medicine container was taken during the time period).

In step 1208, the controller 106 determines a reward for the patient 104 based on the patient 104's compliance level (or levels); and in step 1210 the controller 106 rewards the patient 104. Exemplary rewards for compliance to a medicine schedule include a lower insurance premium, a lower insurance deductible, a lower insurance co-payment, reimbursement for the price of one or more medicines, a free office visit with a doctor (e.g., the doctor that prescribed the medicine schedule), entry in a sweepstakes, money, prizes, points (or some sort of alternative currency), discounts on products, coupons, etc.

In at least one embodiment, the reward may be chosen from a list of available rewards, and the reward may be chosen by an insurance company (e.g., by the insurance company that employs the controller 106), by the patient 104, by a doctor (e.g., by the doctor that prescribed one or more of the medicines taken by the patient 104), etc. The reward may be chosen for the patient 104 based on the patient's prior compliance history. For example, if the patient 104 has a poor compliance history, the patient may be offered a larger reward (e.g., so as to provide a greater incentive for the patient 104 to comply).

The reward may be based on the patient's level of compliance. If the controller 106 employs a gradated compliance level scale, the offered rewards may be similarly gradated (e.g., a patient having a compliance level of 86% may be rewarded with $86 out of a possible $100). Compliance levels may be divided into ranges and a patient may be rewarded based on the range in which the patient's compliance level falls. For example, a 90%-100% compliance level may be rewarded by cash; a 75%-90% compliance level may be rewarded by a reduction in insurance premiums; a 50%-75% compliance level may be rewarded by a sweepstakes entry; and a 50% or lower compliance level may not be rewarded. If the controller 106 employs a "binary" compliance level (e.g., wherein a patient either is in compliance or is not in compliance), a binary reward scheme may be employed (e.g., wherein a patient is charged a $20 insurance co-payment if the patient is not in compliance and a $2 insurance co-payment if the patient is in compliance). A patient also may be penalized for non-compliance, and whether or not a patient is in compliance may depend on other factors (e.g., whether the patient used brand name or generic medicines).

Separate rewards may be provided for compliance with a proximity requirement and for compliance with a requirement for taking medicines. For example, if a patient keeps all of the patient's medicine containers together at all times, but on several occasions neglects to take one of the medicines within one of the medicine containers, the patient may receive a reward (e.g., $50) for keeping the medicine containers together. However, if the patient had not failed to take the one medicine (e.g., if the patient had complied with the patient's requirement for taking medicines), the patient would have received an additional reward (e.g., the patient's insurance premium would have been decreased by $100). Any other rewards/rewarding schemes may be similarly employed, and in return for receiving a reward (or the right to receive a reward) for complying with a schedule for taking medicines, the patient 104 may agree to pay for any illness resulting from non-compliance. Note that in general, and as stated previously, the compliance monitoring device 102 need only track and provide proximity information regarding medicine containers to the controller 106 as described below with reference to FIG. 13.

Second Exemplary Operation of the Controller 106

Figure 13:
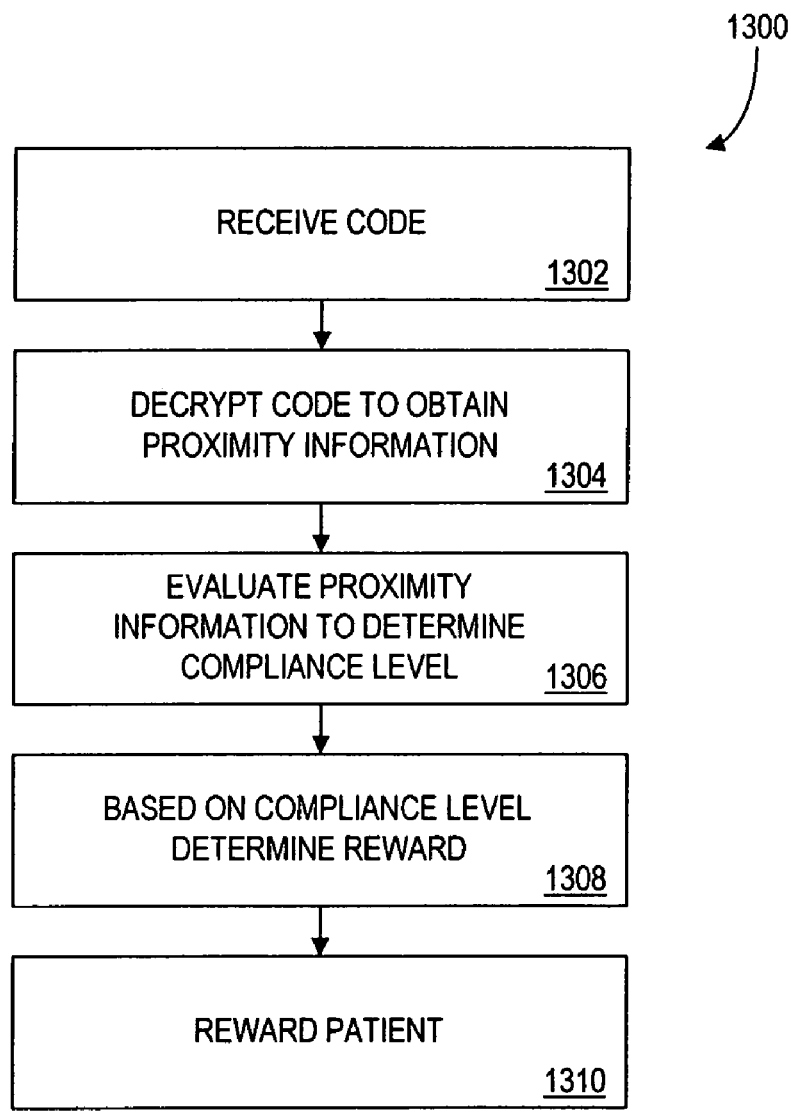
FIG. 13 is a flow chart of a second exemplary process by which a controller of the novel compliance system of FIGS. 1A-8 receives proximity information from a patient and rewards the patient based on the received proximity information.

FIG. 13 is a flow chart of a second exemplary process 1300 by which the controller 106 receives proximity information from the patient 104 (or from the compliance monitoring device 102) and rewards the patient 104 based on the received information. The second exemplary process 1300 of FIG. 13 is similar to the first exemplary process 1200 of FIG. 12, with exception that proximity information is received by the controller 106 (rather than compliance data as in the first exemplary process 1200).

With reference to FIG. 13, the process 1300 begins in step 1302 when the controller 106 receives a code that represents proximity information collected by the compliance monitoring device 102. In at least one embodiment of the invention, the code is sent to the controller 106 from the patient 104 or from the compliance monitoring device 102 in step 1112 of process 1100 of FIG. 11. In general the code may be received from any party and/or from any device (as previously described with reference to the process 1200).

In step 1304, the controller 106 decrypts the received code to determine the proximity information collected by the compliance monitoring device 102. The code may be decrypted by employing a decryption algorithm to recover the pre-encryption proximity information, or if the code was encrypted using a one-way function (e.g., a one-way hash function), rather than decrypting the code, the controller 106 may compare the received code with at least one code corresponding to acceptable proximity information (e.g., an acceptable duration of time the medicine containers were separated). The code received by the controller 106 may include other information that may be employed by the controller 106 to compute a compliance level such as, for example, (1) the amount of each medicine taken by the patient 104; (2) the time each medicine was taken; (3) various physical indications of the patient 104 (e.g., the patient 104's blood pressure, the patient 104's heart rate, the patient 104's blood glucose level, etc.) that may indicate whether or not the patient 104 has taken one or more medicines; and/or (4) any other information for determining whether the patient 104 has complied with a medicine schedule.

In step 1306, the controller 106 evaluates the decrypted proximity information (and any other information provided with the proximity information) to determine one or more levels of compliance of the patient 104 to a medicine schedule. For example, the controller 106 may compare the received proximity information (or any other information provided with the proximity information) to information previously sent to the controller 106 (e.g., a prescribed method for taking each medicine or medicines, the purpose of each medicine, interactions of each medicine with other medicines, or other information sent to the controller 106 in step 904). Any of the previously described methods for computing one or more compliance levels may be employed by the controller 106 to determine one or more levels of compliance of the patient 104.

In step 1308, the controller 106 determines a reward for the patient 104 based on the patient 104's compliance level (or levels); and in step 1310 the controller 106 (or an insurance company that employs the controller 106) rewards the patient 104.

The foregoing description discloses only exemplary embodiments of the invention, modifications of the above disclosed apparatus and methods which fall within the scope of the invention will be readily apparent to those of ordinary skill in the art. For instance, in at least one embodiment of the invention, a group (e.g., a family) may "enroll" in an insurance company's reward program. In order to be rewarded, all members of the group must comply to a schedule for taking one or more medicines (e.g., each member of the group must comply to a medicine schedule for that member). In this manner, the members of the group may enforce each other's compliance. In embodiments wherein a party must call in a code (e.g., a code that provides proximity information and/or compliance data), each member of the group may call in the member's own code, or a composite code may be generated for the entire group and the code may be called in by one party. A multi-tiered reward program may be employed wherein each member of the group receives one reward for compliance to the member's own medicine schedule/proximity requirement and a second reward if the group as a whole is in compliance.

As stated, a central monitoring unit such as the meta-container 102b, the mini-container 102c, a patient's personal computer or laptop computer, etc., may be provided that can communicate with all of the medicine containers. In such an embodiment, each medicine container may employ only an inactive communication element (e.g., a memory device that stores information relating to the medicine stored within the medicine container). The stored information may include information such as, for example, the number of times that a cap of the medicine container was opened and/or closed, or other information gathered by various sensors on/in the medicine container. The central monitoring unit then may poll the memory device of each medicine container to receive the information stored within each medicine container. Whether a proximity requirement of an insurance company is satisfied may be determined based on whether a plurality of medicine containers are "plugged-into" the meta-container 102b or the mini-container 102c.

Multiple central monitoring units may be employed such as multiple meta- and mini-containers 102b, 102c. Because some medicines may require refrigeration, it may not be possible to keep all medicine containers within communication range. Accordingly, a plurality of central monitoring units may be desirable (e.g., one central monitoring unit that can be refrigerated and one central monitoring unit that can be stored within a medicine cabinet). Alternatively, a central monitoring unit may be provided with a refrigerated compartment for storing medicines/medicine containers that require refrigeration.

Note that once a medicine container is empty, the medicine container may be refilled (e.g., by a pharmacist), may be recycled and/or may be reprogrammed for a different medicine. For example, new data corresponding to a different medicine may be written into the container database 712 of the medicine container.

In addition to determining information regarding the distances between medicine containers, the local positioning system 714 (e.g., a global positioning system) of a medicine container may be employed to assist the patient 104 in finding the medicine container (e.g., if the medicine container is misplaced, if the patient needs quick access to the medicine container, etc.).

While the present invention has been described primarily with reference to medicine containers such as pill bottles, it will be understood that the invention may be employed with other types of medicine containers. For example, one or more embodiments of the invention may be employed with micro-needle based devices such as those manufactured by Kumetrix, Inc. of Union City, Calif. (see, for example, www.kumetrix.com). Micro-needle based devices are typically formed by semiconductor device manufacturing techniques, and are capable of delivering (e.g., painlessly) medicines into a patient's blood stream and of sampling and monitoring a patient's blood to detect, for example, glucose levels (e.g., for diabetics), lactate levels (e.g., so as to detect internal bleeding, trauma, shock, etc.), pesticide levels, nerve gas levels, etc. In accordance with one or more embodiments of the invention, micro-needle based devices may be provided that can, for example: (1) wirelessly communicate with one another and/or with a central monitoring device (e.g., by providing each micro-needle based device with a passive or active transceiver); (2) administer predetermined doses of medicine to a patient (e.g., by providing each micro-needle based device with one or more pumps and/or reservoirs); (3) communicate to one another that a dose of medicine has been administered to a patient; (4) monitor patient compliance (e.g., sample blood of the patient to confirm that a dose of medicine was administered to the patient); (5) ensure that incompatible medicines are not administered (e.g., by communicating information about when medicine doses are to be or have been administered to a patient amongst the micro-needle based devices employed by the patient); and/or (6) perform any of the other features described previously with reference to FIGS. 1A-13.

The compliance monitoring device 102 may monitor the time that each medicine stored within one of the inventive medicine containers is to be taken (e.g., in compliance with a prescribed medicine schedule), and may communicate this information to the relevant medicine container so that the medicine container notifies the patient (e.g., via the display 120, via a light-emitting-diode (LED), via an audible tone, etc.,) that the patient should take the medicine stored within the container. The amount of each medicine to be taken may also be identified (see, for example, medicine container 112 in FIG. 1B). Likewise, a medicine container may, based on medicine compatibility information stored within the medicine container and/or within the compliance monitoring device 102, notify or warn a patient that the patient should not take a medicine (e.g., because the patient has already taken or is about to take another incompatible medicine). A notification that a medicine should or should not be taken may be communicated by other mechanisms such as via a pager or by broadcasting the notification over a radio or a television.

Each medicine container that contains an incompatible medicine may "lock" to prevent access to the medicine stored within the medicine container (e.g., until such a time that the patient may safely consume the medicine). Medicine containers similarly may lock when medicine containers are out of range of one another. Previously incorporated U.S. Pat. No. 5,852,590 to de la Huerga discloses locking mechanisms that may be employed with the medicine containers of the present invention. In at least one embodiment of the invention, a medicine container may provide an electrical shock to a patient if the patient attempts to open the medicine container at an inappropriate time (e.g., after taking a different, incompatible medicine). In another embodiment, when medicine containers are out of range of one another, each medicine container may still communicate with the central monitoring device 102 and/or with the controller 106 via a telephone network, via a cellular network, via the Internet or via an other communication means. Further, each medicine container may be configured so that the medicine containers "interlock" (e.g., to ensure that the containers remain proximate); and compliance to a proximity requirement may be monitored graphically and/or visually (e.g., by having a WEB-based camera that provides a video image of the medicine containers to the controller 106).

The patient's medical history may also be included in the information that is programmed into the medicine containers, the compliance monitoring device 102 and/or the controller 106. Further, the medicine containers, the compliance monitoring device 102 and/or the controller 106 may be configured to receive (e.g., wirelessly or by any other means) test results from separate monitoring devices (e.g., from an in-home monitoring kit that monitors a blood glucose level of a patient, from a pregnancy test that identifies whether a patient is pregnant, etc.). In this manner, the medicine containers, the compliance monitoring device 102 and/or the controller 106 may determine, based at least in part on the test results from a separate monitoring device, whether a party should or should not take a medicine. For example, if a test indicates that a patient is pregnant, one or more of the medicine containers may "lock" to prevent the patient from accessing one or more medicines. The compliance monitoring device 102 also may communicate the test results to a third party (e.g., an insurance company, a doctor, a pharmacist, etc.).

If a patient employs a plurality of the inventive medicine containers, a first of which stores a first medicine, a second of the medicine containers and/or the central monitoring device 102 may communicate with a doctor that prescribed the first medicine, with a pharmacy that provided the first medicine or with any other relevant party so as to provide information regarding a second medicine stored within the second medicine container. For example, if a first medicine container that contains a first medicine prescribed by a first doctor is placed proximate a second medicine container that contains a second medicine prescribed by a second doctor, the first and the second medicine containers may communicate with one another (e.g., to exchange information regarding the medicine stored within each medicine container as previously described), the first medicine container may communicate the presence of the second medicine to the first doctor, and the second medicine container may communicate the presence of the first medicine container to the second doctor. Schedules for taking each medicine, the reason for prescribing each medicine and any other information also may be communicated.

Note that if a patient fails to comply to a medicine schedule, the data supplied to the controller 106 by the central monitoring device 102 may be an alarm rather than compliance data (e.g., an alarm that indicates that the patient has overdosed). The receipt of an alarm by the controller 106 may trigger an emergency response (e.g., the controller 106 may call an ambulance), or the controller 106 may issue a warning to the patient and/or to the patient's doctor.

While the present invention has been described primarily with reference to a "proximity requirement" for two or more medicine containers that may communicate wirelessly, it will be understood that an insurance company and/or some other relevant party similarly may impose a "communication requirement" that requires, for example, that two or more medicine containers merely be capable of communicating with one another during a pre-determined time period rather than be proximate one another. For example, medicine containers may be configured so as to communicate with one another via a telephone network such as a publicly switched telephone network (PSTN), via a cable network, via an intranet, via an extranet, via the Internet, via an Internet-based telephone network, or via any other communication medium (e.g., a radio frequency link, a microwave link, an optical link, etc.) that does not necessarily require the medicine containers to be proximate one another.

Each medicine may have a priority ranking, so that if there are conflicting medicines, the medicine with the highest priority ranking is incorporated into a medicine schedule before any of the other medicines. For example, assume a patient is taking heart medicine, anti-nausea medicine, and an anti-depressant medicine that are ranked 1, 2 and 3 in importance, respectively. The heart medicine is to be taken every 3 hours, the anti-nausea medicine is to be taken every 4 hours and the anti-depressant medicine is to be taken every 6 hours. The heart medicine and the anti-nausea medicine cannot be taken together (e.g., the patient should wait at least one hour after taking one of the medicine before taking the other medicine).

The patient starts by taking the heart medicine and the anti-depressant medicine at 12:00 p.m. At 1:00 p.m., the patient takes the anti-nausea medicine. At 3:00 p.m., the patient takes the heart medicine again. At 5:00 p.m., the patient takes the anti-nausea medicine. At 6:00 p.m. the patient takes the heart medicine and the anti-depressant medicine. At 9:00 p.m., the patient should take both the heart medicine and the anti-nausea medicine; however, the heart medicine and the anti-nausea medicine are incompatible. Because the heart medicine has the higher priority, the medicine container that stores the heart medicine and/or the medicine container that stores the anti-nausea medicine may indicate to the patient that the anti-nausea medicine is not to be taken at this time, but that the heart medicine is to be taken at this time. Accordingly, the patient takes the heart medicine. Then at 10:00 p.m., the anti-nausea medicine container indicates to the patient that the patient should take the nausea medicine.

Accordingly, while the present invention has been disclosed in connection with the exemplary embodiments thereof, it should be understood that other embodiments may fall within the spirit and scope of the invention as defined by the following claims.

What is claimed is:

1. A method comprising:
   receiving a signal; and
   determining whether a first container for storing a first medicine was positioned so as to wirelessly communicate with a second container for storing a second medicine based at least in part on the signal.

2. The method of claim 1 wherein receiving a signal comprises receiving the signal from a device that monitors at least an indicator of whether the first container and the second container are positioned so as to wirelessly communicate.

3. The method of claim 2 wherein the device comprises at least one of the first container and the second container.

4. The method of claim 2 wherein receiving the signal from a device that monitors at least an indicator of whether the first container and the second container are positioned so as to wirelessly communicate comprises polling the device.

5. The method of claim 1 wherein receiving a signal comprises receiving a signal from at least one of a representative of a pharmacy, a representative of a medical facility and a party that is to take at least one of the first and the second medicines.

6. The method of claim 1 wherein receiving a signal comprises receiving a code.

7. The method of claim 6 wherein the code is an encrypted code.

8. The method of claim 7 wherein determining whether a first container for storing a first medicine was positioned so as to wirelessly communicate with a second container for storing a second medicine based at least in part on the signal comprises decrypting the encrypted code.

9. The method of 1 wherein determining whether a first container for storing a first medicine was positioned so as to wirelessly communicate with a second container for storing a second medicine based at least in part on the signal comprises determining whether the signal indicates that the first container for storing the first medicine was positioned so as to wirelessly communicate with the second container for storing the second medicine during a pre-determined time period.

10. The method of 1 further comprising determining if at least one party has complied with a schedule for taking the first medicine and the second medicine based at least in part on the received signal.

11. The method of claim 10 wherein determining if at least one party has complied with a schedule for taking the first medicine and the second medicine based at least in part on the received signal comprises:

receiving first information regarding a prescribed schedule for taking the first medicine and the second medicine;
receiving second information regarding a schedule for taking the first medicine and the second medicine adhered to by the at least one party;
comparing the first information to the second information; and
generating at least an indicator of a level to which the at least one party has complied with a schedule for taking the first medicine and the second medicine.

12. The method of claim 11 wherein obtaining first information regarding the first medicine and the second medicine comprises obtaining the first information from at least one of a representative of a pharmacy, a representative of a medical facility and a representative of a manufacturer of at least one of the first and the second medicines.

13. An apparatus comprising:
   a communication device adapted to receive a signal;
   a processor coupled to the communication device, the processor adapted to obtain the signal via the communication device; and
   a computer program, the computer program executable by the processor so as to direct the processor to:
      receive the signal; and
      determine whether a first container for storing a first medicine was positioned so as to communicate with a second container for storing a second medicine based at least in part on the signal.

14. The apparatus of claim 13 wherein the computer program further includes program code executable by the processor so as to direct the processor to determine if at least one party has complied with a schedule for taking the first medicine and the second medicine based at least in part on the received signal.

15. A system for rewarding at least one party for complying with a schedule for taking a first medicine and a second medicine comprising:
   a first container adapted to store a first medicine;
   a second container adapted to store a second medicine and to communicate with the first container;
   a compliance monitoring device adapted to:
      communicate with at least the first container;
      determine, based on at least a communication with the first container, whether the first container is positioned so as to communicate with the second container;
      generate data based at least in part on whether the first container is positioned so as to communicate with the second container; and
      output the data; and
   a server adapted to:
      receive the data output by the compliance monitoring device; and
      reward at least one party based on the received data.

16. The system of claim 15 wherein the server is further adapted to:
   determine a level to which the at least one party has complied with a schedule for taking the first medicine and the second medicine based at least in part on the data received from the compliance monitoring device; and
   reward the at least one party based on the level.

17. A method for rewarding a party for complying with a medicine schedule comprising:
   receiving information regarding whether at least one first container for storing a first medicine was able to communicate with at least one second container for storing a second medicine during a pre-determined time period;

determining a level to which the party complied with a medicine schedule based on the information; and rewarding the party based on the level.

18. The method of claim 17 wherein the information comprises encrypted information.

19. A computer program product comprising:
a medium readable by a computer, the computer-readable medium having:
program code adapted to obtain information regarding whether at least one first container for storing a first medicine was able to communicate with at least one second container for storing a second medicine during a pre-determined time period;
program code adapted to determine a level to which the party complied with a medicine schedule based on the information; and
program code adapted to determine a reward for the party based on the level.

20. The computer program product of claim 19, in which the reward comprises a discount on a product.

21. An apparatus comprising:
means for obtaining information that identifies whether at least one first container for storing a first medicine was able to communicate with at least one second container for storing a second medicine during a pre-determined time period; and
means for rewarding a party based on the information.

22. A method comprising:
receiving a signal from a device that monitors whether a first container for storing a first medicine was positioned so as to communicate with a second container for storing a second medicine; and
determining if at least one party has complied with a schedule for taking the first medicine and the second medicine based at least in part on the received signal.

23. The method of claim 22,
in which the received signal indicates whether the first container for storing the first medicine was positioned so as to communicate with the second container for storing the second medicine.

24. The method of claim 22,
in which determining if at least one party has complied with a schedule for taking the first medicine and the second medicine based at least in part on the received signal comprises determining whether the first container was positioned so as to communicate with the second container based at least in part on the received signal.

25. The method of claim 22 in which determining if at least one party has complied with a schedule for taking the first medicine and the second medicine based at least in part on the received signal comprises:
receiving first information regarding the first medicine and the second medicine;
determining second information regarding the first medicine and the second medicine based on the received signal; and
generating at least an indicator of a level to which the at least one party has complied with a schedule for taking the first medicine and the second medicine based on the first and the second information.

26. The method of claim 22, further comprising:
rewarding the at least one party if the at least one party has complied with the schedule for taking the first medicine and the second medicine.

27. The method of claim 26, in which rewarding the at least one party comprises:
determining a level to which the at least one party has complied with the schedule for taking the first medicine and the second medicine; and
rewarding the at least one party based on the level.

28. The method of claim 26 in which rewarding the at least one party comprises:
providing the at least one party with a list of rewards;
receiving a selection of one of the listed rewards; and
providing the selected reward to the at least one party.

29. The method of claim 26, in which rewarding the at least one party comprises:
providing the at least one party with a reward selected by at least one of:
a representative of an insurance company, and
a representative of a medical facility.

30. The method of claim 26, in which rewarding the at least one party comprises:
determining a previous level to which the at least one party has complied with the schedule for taking the first medicine and the second medicine;
determining a reward based at least in part on the previous level; and
providing the at least one party with the reward.

31. The method of claim 26, in which rewarding the at least one party comprises:
providing the at least one party with a first reward based on a distance between the first container and the second container; and
providing the at least one party with a second reward based on at least one other indicator that the at least one party has complied with the schedule for taking the first medicine and the second medicine.

32. The method of claim 22, further comprising:
penalizing the at least one party if the at least one party has not complied with the schedule for taking the first medicine and the second medicine.

33. The method of claim 32 in which penalizing the at least one party comprises:
charging the at least one party for at least a portion of a treatment of an illness,
in which the illness results at least in part from the at least one party not complying with the schedule for taking the first medicine and the second medicine.

34. A method comprising:
a step for obtaining information that identifies whether at least one first container for storing a first medicine was able to communicate with at least one second container for storing a second medicine during a pre-determined time period; and
a step for rewarding a party based on the information.

* * * * *